(12) United States Patent
Kakefuda et al.

(10) Patent No.: US 6,576,455 B1
(45) Date of Patent: Jun. 10, 2003

(54) STRUCTURE-BASED DESIGNED HERBICIDE RESISTANT PRODUCTS

(75) Inventors: Genichi Kakefuda, Yardley, PA (US); Karl-Heinz Ott, Lawrenceville, NJ (US); Jae-Gyu Kwagh, Fairless Hills, PA (US); Gerald W. Stockton, Yardley, PA (US)

(73) Assignee: BASF Corporation, Research Triangle Park, NC (US)

( * ) Notice: Subject to any disclaimer, the term of this patent is extended or adjusted under 35 U.S.C. 154(b) by 0 days.

(21) Appl. No.: 09/367,512

(22) PCT Filed: Apr. 19, 1996

(86) PCT No.: PCT/US96/05782

§ 371 (c)(1),
(2), (4) Date: Aug. 17, 2000

(87) PCT Pub. No.: WO96/33270

PCT Pub. Date: Oct. 24, 1996

Related U.S. Application Data

(60) Continuation-in-part of application No. 08/455,355, filed on May 31, 1995, now Pat. No. 5,928,937, which is a division of application No. 08/426,125, filed on Apr. 20, 1995, now Pat. No. 5,853,973.

(51) Int. Cl.$^7$ ................................................. C12N 9/88
(52) U.S. Cl. ..................... 435/232; 536/23.2; 435/189; 435/183
(58) Field of Search ................................. 435/232, 183, 435/189; 536/23.2

(56) References Cited

U.S. PATENT DOCUMENTS 5,767,361 A * 6/1998 Dietric ........................ 800/205

OTHER PUBLICATIONS

Mosimann et al. "A critical assessment of comparative molecular modeling . . . " Protein Struc. Funct. and Genet. (1995) 23, 301–317.*

Yadav et al. "Single amino acid substitution in the enzyme acetolactate synthase . . . " Proc. Natl. Acad. Sci. U. S. A. 83, 4418–4422.*

Hattori et al. "Multiple resistance to sulfonylureas and imidazolinones conferred by . . . "Mol. Gen. Genet. (1992) 232, 167–173.*

Sathasivan et al. "Molecular basis of imidazolinone herbicide resistance . . . " (1991), 97, 1044–1050.*

* cited by examiner

*Primary Examiner*—Nashaat T. Nashed
(74) *Attorney, Agent, or Firm*—Sutherland Asbill & Brennan LLP

(57) ABSTRACT

Disclosed herein are structure-based modelling methods for the preparation of acetohydroxy acid synthase (AHAS) variants, including those that exhibit selectively increased resistance to herbicides such as imidazoline herbicides and AHAS inhibiting herbicides. The invention encompasses isolated DNAs encoding such variants, vectors that include the DNAs, and methods for producing the variant polypeptides and herbicide resistant plants containing specific AHAS gene mutations. Methods for weed control in crops are also provided.

7 Claims, 26 Drawing Sheets

```
A ─────────────────────────────────────────────────────────────── A

*1    * GSAASPAMP*10  *MAPPATPLRP*20  *WGPTDPRKGA*

*60   *TRSPVIANHL*70  *FRHEQGEAFA*80  *ASGYARSSGR*
                    Arg128      Phe135
*120  *AITGQVPRRM*130 *IGTDAFQETP*140 *IVEVTRSITK*

*180  *LVDIPKDIQQ*190 *QMAVPVWDKP*200 *MSLPGYIARL*

*240  *ARSGEELRRF*250 *VELTGIPVTT*260 *TLMGLGNFPS*

*300  *GVRFDDRVTG*310 *KIEAFASRAK*320 *IVHVDIDPAE*

*360  *SKKSFDFGSW*370 *NDELDQQKRE*380 *FPLQYKTSNE*

*420  *WAAQYYTYKR*430 *PRQWLSSAGL*440 *GAMGFGLPAA*

*480  *IRIENLPVKV*490 *FVLNNQHLGM*500 *VVQWEDRFYK*

*540  *PAVRVTKKNE*550 *VRAAIKKMLE*560 *TPGPYLLDII*
```

Met53

30 *DILVESLERC*40 *GVRDVFAYPG*50 *GASMEIHQAL

90 *VGVCIATSGP*100*GATNLVSALA*110*DALLDSVPMV

150*HNYLVLDVDD*160*IPRVVQEAFF*170*LASSGRPGPV

210*PKPPATELLE*220*QVLRLVGESR*230*RPVLYVGGGC

270*DDPLSLRMLG*280*MHGTVYANYA*290*VDKADLLLAL

330*IGKNKQPHVS*340*ICADVKLALQ*350*GMNALLEGST

390*EIQPQYAIQV*400*LDELTKGEAI*410*IGTGVGQHQM

450*AGASVANPGV*460*TVVDIDGDGS*470*FLMNVQELAM

510*ANRAHTYLGN*520*PENESEIYPD*530*FVTIAKGFNI

570*VPHQEIVLPM*580*IPSGGAFKDM*590*ILDGDGRTVY

FIG. 2a

```
POX        *         *             *24 *    TNILAGA*31 *AVIKVLEAWG*41 *VDHLYGIPGG*51 *SINSIMDALS
                                            |||||||    ||||||| ||    ||||||||||    || ||||||||
AHAS_pred *1 *GSAASPAMPM*11 *APPATPLRPW*21 *GPTDPRKGAD*31 *ILVESLERCG*41 *VRDVFAYPGG*51 *ASMEIHQALT POX       *61 *AERDRIHYIQ*71 *VRHEEVGAMA*81 *AAADAKLTGK*91 *IGVCFGSAGP*101*GGTHLMNGLY*111*DAREDHVPVL
              |  |||||||     |||||||||      ||||||||||     |||||||||    |||||||||    |||  ||||
AHAS_pred *61 *RS PVIANHL*70 *FRHEQGEAFA*80 *ASGYARSSGR*90 *VGVCIATSGP*100*GATNLVSALA*110*DALLDSVPMV POX       *121*ALIGQFGTTG*131*MNMDTFQEMN*141*ENPIYADVAD*151*YNVTAVNAAT*161*LPHVIDEAIR*171*RAYAHQ GVA
              ||||||||||    ||||||||||    |  |||| |||    ||| |||||||    ||||| |||    ||||||  |||
AHAS_pred *120*AITGQVPRRM*130*IGTDAFQETP*140*IVEVTRSITK*150*HNYLVLDVDD*160*IPRVVQEAFF*170*LASSGRPGPV POX       *180*VVQIPVDLP *189*WQQISAEDWY*199*ASANN  YQT*207*PLLPEPDVQA*217*VTRLTQTLLA*227*AERPLIYYGI
              |||||||||     ||||||||||    ||||    |||    ||||||||||    ||  ||||||    ||||||||||
AHAS_pred *180*LVDIPKDIQ *189* QQMAVPVWD*198*KPMSLPGYIA*208*RLPKPPATEL*218*LEQVLRLVGE*228*SRRPVLYVGG POX       *237*GARKAGKELE*247*QLSKTLKIPL*257*MSTYPAKGIV*267*ADRYPAYLGS*277*ANRVAQKPAN*287*EALAQADVVL
              |  |||||||    |||| |||||    ||||| |||    |||||  ||    |||||  ||    ||||||||||
AHAS_pred *238*GCARSGEELR*248*RFVELTGIPV*258*TTTLMGLGNF*268*PSDDPLSLRM*278*LGMHGTVYAN*288*YAVDKADLLL A─────────                                                                                      ─A
```

FIG. 2b

```
POX        *297*FVGNNY    PF*305*AEVSKAFKNT*315*RYFLQIDIDP*325*AKLGKRHKTD*335*IAVLAD    A*342*QKTLAAILAQ
               ||| ||  ||        ||||||||||       ||||||||||       ||  |||||| |||       ||||||       |||||||||||
AHAS_pred  *298*ALGVRFDDRV*308*TGKIEAFASR*318*AKIVHVDIDP*328*AEIGKNKQPH*338*VSICADVKLA*348*LQGMNALLEG POX        *352*VSEREST    *359*PWWQANLANV*369*KNWRAYLASL*379*EDKQEGPLQA*389*YQVLRAVNKI*399*AEPDAIYSID
               |||||                ||| |||       |||                ||| |||       ||||||||||       ||||||||||
AHAS_pred  *358*STSKKSFDFG*368*SWNDELDQQK*378*REFPLGYKTS*388*NEE    IQP*394*QYAIQVLDEL*404*TKGEAIIGTG POX        *409*VGDINLNANR*419*HLKLTPSNRH*429*ITSNLFATMG*439*VGIPGAIAAK*449*LNYPERQVFN*459*LAGDGGASMT
               |||||| |||       |||| |||       ||||| ||||       |||||||||       ||| ||||||       |||||  ||
AHAS_pred  *414*VGQHQMWAAQ*424*YYTYKRPRQW*434*LSSAGLGAMG*444*FGLPAAAGAS*454*VANPGVTVVD*464*IDGDGSFLMN POX        *469*MQDLVTQVQY*479*HLPVINVVFT*489*NCQYGFIKDE*499*QEDTNQNDFI*509*GVEFNDID   F*518*SKIADGVHMQ
               |||||||||||       |||| |||       |||  |||||       ||| |||       ||  ||||||       |||   ||
AHAS_pred  *474*VQELAMIRIE*484*NLPVKFVLN*494*NQHLGMVVQW*504*EDRFYKANRA*514*HTYLGNPENE*524*SEIYPDFVTI POX        *528*AFRVNKIEQL*538*PDVFEQAKAI*548*AQHEPVLIDA*558*VITGDRPLPA*568*EKLRLDSAMS*578*SAADIEAFKQ
               |  ||||||||       |||  ||||       |||||| |||       ||||||||||       ||  |||||       ||||||||||
AHAS_pred  *534*AKGFNIPAVR*544*VTKKNEVRAA*554*IKKMLETPGP*564*YLLDIIVPHQ*574*EHVLPMIPSG*584*GAFKDMILDG POX        *588*RYEAQDLQPL*598*STYLKQFGLD*608*D
               |||||                                *     *     *
AHAS_pred  *594*DGRTVY        *     *
```

FIG. 5a

```
             1                                                              50
Pac751       ..........  ..........  ..........  ..........  ..........
Maizeals2    ..........  ..........  ..........  ..MATAAAAS  TALTGATTAA
Maizeals1    ..........  ..........  ..........  ..MATAATAA  AALTGATTAT
Tobac1       MAAA...APS  PSSSAFSKTL  SPSSSTSSTL  LPRSTFPFPH  HPHKTTPPPL
Tobac2       MAAA...AAA  PSPS.FSKTL  SSSSSKSSTL  LPRSTFPFPH  HPHKTTPPPL
Athcsr12     MAAATTTTTT  SSSISFSTKP  SPSSSKSPLP  ISRFSLPFSL  NPNKSSSSSR
Bnaal3       MAAA...TS   SSPISLTAKP  ...SSKSPLP  ISRFSLPFSL  TPQKPSSRLH
Bnaal2       ........M   ASFSFFGTIP  S.....SPTK  ASVFSLPVSV  TTLPSFPRRR
Consensus    MAAA---ATS  -S-SSFS--P  SPSSSKSPT-  -SRFTLPFS-  TPLK--P---

51                                                             100
Pac751       ..........  .GSAAASPAMP  MAPPATPLRP  WGPTDPRKGA
Maizeals2    PKARRRAHLL  ATRRALAAPI   RCSAAASPAMP MAPPATPLRP WGPTDPRKGA
Maizeals1    PKSRRRAHHL  ATRRALAAPI   RCSALSRATP  TAPPATPLRP  WGPNEPRKGS
Tobac1       HLTHTHIHIH  SQRRRFTISN   VISTNQKVSQ  TEKTETFVSR  FAPDEPRKGS
Tobac2       HLTPT..HIH  SQRRRFTISN   VISTTQKVSE  TQKAETFVSR  FAPDEPRKGS
Athcsr12     RRGIKSSSPS  SISAVLNTTT   NVTTTPSPTK  PTKPETFISR  FAPDQPRKGA
Bnaal3       R........PL AISAVLNSPV   NV....APEK  TDKIKTFISR  YAPDEPRKGA
Bnaal2       ........AT  RVSVSANSKK   DQDRTAS..R  RENPSTFSSK  YAPNVPRSGA
Consensus    --TR-RAH-L  -IRR-LN-PI   --S-TS-A-P  T-KP-TF-SR  -APDEPRKGA
```

FIG. 5b

```
           101
Pac751     DILVESLERC GVRDVFAYPG GASMEIHQAL TRSPVIANHL FRHEQGEAFA
Maizeals2  DILVESLERC GVRDVFAYPG GASMEIHQAL TRSPVIANHL FRHEQGEAFA
Maizeals1  DILVEALERC GVRDVFAYPG GASMEIHQAL TRSPVIANHL FRHEQGEAFA
Tobac1     DVLVEALERE GVTDVFAYPG GASMEIHQAL TRSSIIRNVL PRHEQGGVFA
Tobac2     DVLVEALERE GVTDVFAYPG GASMEIHQAL TRSSIIRNVL PRHEQGGVFA
Athcsr12   DILVEALERQ GVETVFAYPG GASMEIHQAL TRSSSIRNVL PRHEQGGVFA
Bnaal3     DILVEALERQ GVETVFAYPG GASMEIHQAL TRSSTIRNVL PRHEQGGVFA
Bnaal2     DILVEALERQ GVDVVFAYPG GASMEIHQAL TRSNTIRNVL PRHEQGGIFA
Consensus  DILVEALER- GV-DVFAYPG GASMEIHQAL TRSSVIRNVL PRHEQGGVFA
                                           ↑
                    EQUIVALENT TO MAIZE MET 53          150

151                                          200
Pac751     ASGYARSSGR VGVCIATSGP GATNLVSALA DALLDSVPMV AITGQVPRRM
Maizeals2  ASGYARSSGR VGVCIATSGP GATNLVSALA DALLDSVPMV AITGQVPRRM
Maizeals1  ASAYARSSGR VGVCIATSGP GATNLVSALA DALLDSVPMV AITGQVPRRM
Tobac1     AEGYARATGF PGVCIATSGP GATNLVSGLA DALLDSVPIV AITGQVPRRM
Tobac2     AEGYARATGF PGVCIATSGP GATNLVSGLA DALLDSVPIV AITGQVPRRM
Athcsr12   AEGYARSSGK PGICIATSGP GATNLVSGLA DALLDSVPLV AITGQVPRRM
Bnaal3     AEGYARSSGK PGICIATSGP GATNLVSGLA DAMLDSVPLV AITGQVPRRM
Bnaal2     AEGYARSSGK PGICIATSGP GAMNLVSGLA DALFDSVPLI AITGQVPRRM
Consensus  AEGYARSSG- PGVCIATSGP GATNLVSGLA DALLDSVP-V AITGQVPRRM
                                                              ↑
                    EQUIVALENT TO MAIZE ARG 128
```

FIG. 5c

```
                              EQUIVALENT TO MAIZE PHE 135
              201                            ↓
Pac751        IGTDAFQETP  IVEVTRSITK  HNYLVLVLDVDD  IPRVVQEAFF  LASSGRPGPV
Maizeals2     IGTDAFQETP  IVEVTRSITK  HNYLVLVLDVDD  IPRVVQEAFF  LASSGRPGPV
Maizeals1     IGTDAFQETP  IVEVTRSITK  HNYLVLVLDVDD  IPRVVQEAFF  LASSGRPGPV
Tobac1        IGTDAFQETP  IVEVTRSITK  HNYLVMDVED   IPRVVQEAFF  LARSGRPGPI
Tobac2        IGTDAFQETP  IVEVTRSITK  HNYLVMDVED   IPRVVREAFF  LARSGRPGPV
Athcsr12      IGTDAFQETP  IVEVTRSITK  HNYLVMDVED   IPRVVREAFF  LARSGRPGPV
Bnaal3        IGTDAFQETP  IVEVTRSITK  HNYLVMDVDD   IPRIIEEAFF  LATSGRPGPV
Bnaal2        IGTDAFQETP  IVEVTRSITK  HNYLVMDVDD   IPRIVQEAFF  LATSGRPGPV
              IGTMAFQETP  VVEVTRTITK  HNYLVMEVDD   IPRIVREAFF  LATSVRPGPV
Consensus     IGTDAFQETP  IVEVTRSITK  HNYLVMDVDD   IPRVVQEAFF  LA-SGRPGPV 251                                                       300
Pac751        LVDIPKDIQQ  QMAVPVWDKP  MSLPGYIARL  PKPPATELLE  QVLRLRLVGESR
Maizeals2     LVDIPKDIQQ  QMAVPVWDKP  MSLPGYIARL  PKPPATELLE  QVLRLRLVGESR
Maizeals1     LVDIPKDIQQ  QMAVPAWDTP  MSLPGYIARL  PKPPATEFLE  QVLRLRLVGESR
Tobac1        LIDVPKDIQQ  QLVIPDWDQP  MRLPGYMSRL  PKLPNEMLLE  QIVRLISESK
Tobac2        LIDVPKDIQQ  QLVIPDWDQP  MRLPGYMSRL  PKLPNEMLLE  QIVRLISESK
Athcsr12      LVDVPKDIQQ  QLAIPNWEQA  MRLPGYMSRM  PKPPEDSHLE  QIVRLISESK
Bnaal3        LVDVPKDIQQ  QLAIPNWDQP  MRLPGYMSRL  PQPPEVSQLG  QIVRLISESK
Bnaal2        LIDVPKDVQQ  QFAIPNWEQP  MRLPLYMSTM  PKPPKVSHLE  QILRLVSESK
Consensus     LVDVPKDIQQ  QLAIPNWDQP  MRLPGYMSRL  PKPPA--LLE  QI-RL-SESK
```

FIG. 5d

```
            301
Pac751      RPVLYVGGGC ARSGEELRRF VELTGIPVTT TLMGLGNFPS DD.PLSLRML
Maizeals2   RPVLYVGGGC AASGEELRRF VELTGIPVTT TLMGLGNFPS DD.PLSLRML
Maizeals1   RPVLYVGGGC AASGEELCRF VELTGIPVTT TLMGLGNFPS DD.PLSLRML
Tobac1      KPVLYVGGGC SQSSEDLRRF VELTGIPVAS TLMGLGAFPT GD.ELSLSML
Tobac2      KPVLYVGGGC SQSSEELRRF VELTGIPVAS TLMGLGAFPT GD.ELSLSML
Athcsr12    KPVLYVGGGC LNSSDELGRF VELTGIPVAS TLMGLGSYPC DD.ELSLHML
Bnaal3      RPVLYVGGGS LNSSEELGRF VELTGIPVAS TLMGLGSYPC ND.ELSLQML
Bnaal2      RPVLYVGGGC LNSSEELRRF VELTGIPVAS TFMGLGSYPC DDEEFSLQML
Consensus   RPVLYVGGGC -NSSEELRRF VELTGIPVAS TLMGLG-FP- DD-ELSLRML 351                                              400
Pac751      GMHGTVYANY AVDKADLLLA LGVRFDDRVT GKIEAFASRA KIVHVDIDPA
Maizeals2   GMHGTVYANY AVDKADLLLA LGVRFDDRVT GKIEAFASRA KIVHVDIDPA
Maizeals1   GMHGTVYANY AVDKADLLLA FGVRFDDRVT GKIEAFAGRA KIVHIDIDPA
Tobac1      GMHGTVYANY AVDSSDLLLA FGVRFDDRVT GKLEAFASRA KIVHIDIDSA
Tobac2      GMHGTVYANY AVDSSDLLLA FGVRFDDRVT GKLEAFASRA KIVHIDIDSA
Athcsr12    GMHGTVYANY AVEHSDLLLA FGVRFDDRVT GKLEAFASRA KIVHIDIDSA
Bnaal3      GMHGTVYANY AVEHSDLLLA FGVRFDDRVT GKLEAFASRA KIVHIDIDSA
Bnaal2      GMHGTVYANY AVEYSDLLLA FGVRFDDRVT GKLEAFASRA KIVHIDIDST
Consensus   GMHGTVYANY AVDKSDLLLA FGVRFDDRVT GKLEAFASRA KIVHIDIDSA
```

FIG. 5e

```
            401                                                           450
Pac751      EIGKNKQPHV  SICADVKLAL  QGMNALLEGS  TSKKSFDFGS  WNDELDQQKR
Maizeals2   EIGKNKQPHV  SICADVKLAL  QGMNALLEGS  TSKKSFDFGS  WNDELDQQKR
Maizeals1   EIGKNKQPHV  SICADVKLAL  QGMNTLLEGS  TSKKSFDFGS  WHDELDQQKR
Tobac1      EIGKNKQPHV  SICADIKLAL  QGLNSILESK  EGKLKLDFSA  WRQELTEQKV
Tobac2      EIGKNKQPHV  SICADIKLAL  QGLNSILESK  EGKLKLDFSA  WRQELTVQKV
Athcsr12    EIGKNKTPHV  SVCGDVKLAL  QGMNKVLENR  AEELKLDFGV  WRNELNVQKQ
Bnaal3      EIGKNKTPHV  SVCGDVKLAL  QGMNKVLENR  AEELKLDFGV  WRSELSEQKQ
Bnaal2      EIGKNKTPHV  SVCCDVQLAL  QGMNEVLENR  RD..VLDFGE  WRCELNEQRL
Consensus   EIGKNKQPHV  SICADVKLAL  QGMN-VLE--  T-KLKLDFGS  WRDELD-QKR 451                                                           500
Pac751      EFPLGYKTSN  EEIQPQYAIQ  VLDELTKGEA  IIGTGVGQHQ  MWAAQYYTYK
Maizeals2   EFPLGYKTSN  EEIQPQYAIQ  VLDELTKGEA  IIGTGVGQHQ  MWAAQYYTYK
Maizeals1   EFPLGYKIFN  EEIQPQYAIQ  VLDELTKGEA  IIATGVGQHQ  MWAAQYYTYK
Tobac1      KHPLNFKTFG  DAIPPQYAIQ  VLDELTNGNA  IISTGVGQHQ  MWAAQYYKYR
Tobac2      KYPLNFKTFG  DAIPPQYAIQ  VLDELTNGSA  IISTGVGQHQ  MWAAQYYKYR
Athcsr12    KFPLSFKTFG  EAIPPQYAIK  VLDELTDGKA  IISTGVGQHQ  MWAAQYYKYR
Bnaal3      KFPLSFKTFG  EAIPPQYAIQ  VLDELTQGKA  IISTGVGQKA  MWAAQFYKYR
Bnaal2      KFPLRYKTFG  EEIPPQYAIQ  LLDELTDGKA  IITTGVGQHQ  MWAAQFYRFK
Consensus   KFPLG-KTFG  E-IPPQYAIQ  VLDELTKG-A  IISTGVGQHQ  MWAAQYY-YK
```

FIG. 5f

```
            501
Pac751      RPRQWLSSAG LGAMGFGLPA AAGASVANPG VTVVDIDGDG SFLMNVQELA
Maizeals2   RPRQWLSSAG LGAMGFGLPA AAGASVANPG VTVVDIDGDG SFLMNVQELA
Maizeals1   RPRQWLSSAG LGAMGFGLPA AAGAAVANPG VTVVDIDGDG SFLMNIQELA
Tobac1      KPRQWLTSGG LGAMGFGLPA AIGAAVGRPD EVVVDIDGDG SFIMNVQELA
Tobac2      KPRQWLTSGG LGAMGFGLPA AIGAAVGRPD EVVVDIDGDG SFIMNVQELA
Athcsrl2    KPRQWLSSGG LGAMGFGLPA AIGASVANPD AIVVDIDGDG SFIMNVQELA
Bnaal3      KPRQWLSSSG LGAMGFGLPA AIGASVANPD AIVVDIDGDG SFIMNIQELA
Bnaal2      KPRQWLSSGG LGAMGFGLPA AMGAAIANPG AVVVDIDGDG SFIMNIQELA
Consensus   KPRQWLSSGG LGAMGFGLPA AIGA-VANP- --VVDIDGDG SFIMNVQELA 551                                              600
Pac751      MIRIENLPVK VFVLNNQHLG MVVQWEDRFY KANRAHTYLG NPENESEIYP
Maizeals2   MIRIENLPVK VFVLNNQHLG MVVQWEDRFY KANRAHTYLG NPENESEIYP
Maizeals1   MIRIENLPVK VFVLNNQHLG MVVQWEDRFY KANRAHTFLG NPENESEIYP
Tobac1      TIKVENLPVK IMLLNNQHLG MVVQWEDRFY KANRAHTYLG NPSNEAEIFP
Tobac2      TIKVENLPVK IMLLNNQHLG MVVQWEDRFY KANRAHTYLG NPSNEAEIFP
Athcsrl2    TIRVENLPVK VLLLNNQHLG MVMQWEDRFY KANRAHTYLG DPAQEDEIFP
Bnaal3      TIRVENLPVK ILLLNNQHLG MVMQWEDRFY KANRAHTFLG DPARENEIFP
Bnaal2      TIRVENLPVK VLLINNQHLG MVLQWEDHFY AANRADSFLG DPANPEAVFP
Consensus   TIRVENLPVK V-LLNNQHLG MVVQWEDRFY KANRAHTYLG NP-NESEIFP
```

FIG. 5g

```
           601                                                               650
Pac751     DFVTIAKGFN  IPAVRVTKKN  EVRAAIKKML  ETPGPYLLDI  IVPHQEHVLP
Maizeals2  DFVTIAKGFN  IPAVRVTKKN  EVRAAIKKML  ETPGPYLLDI  IVPHQEHVLP
Maizeals1  DFVAIAKGFN  IPAVRVTKKS  EVHAAIKKML  EAPGPYLLDI  IVPHQEHVLP
Tobac1     NMLKFAEACG  VPAARVTHRD  DLRAAIQKML  DTPGPYLLDV  IVPHQEHVLP
Tobac2     NMLKFAEACG  VPAARVTHRD  DLRAAIQKML  DTPGPYLLDV  IVPHQEHVLP
Athcsr12   NMLLFAAACG  IPAARVTKKA  DLREAIQTML  DTPGPYLLDV  IVPHQEHVLP
Bnaal3     NMLQFAGACG  IPAARVTKKE  ELREAIQTML  DTPGPYLLDV  ICPHQEHVLP
Bnaal2     DMLLFAASCG  IPAARVTRRE  DLREAIQTML  DTPGPFLLDV  ICPHQEHVLP
Consensus  -ML-FAKACG  IPAARVTKK-  -LRAAIQKML  DTPGPYLLDV  IVPHQEHVLP 651                              673
Pac751     MIPSGGAFKD  MILDGDGRTV  Y...
Maizeals2  MIPSGGAFKD  MILDGDGRTV  Y*.
Maizeals1  MIPSGGAFKD  MILDGDGRTV  Y*.
Tobac1     MIPSGGAFKD  VITEGDGRTV  Y*.
Tobac2     MIPSGGAFKD  VITEGDGRSS  Y*.
Athcsr12   MIPSGGAFKD  VITEGDGRSS  Y*.
Bnaal3     MIPNGGTFND  VITEGDGRIK  Y*E
Bnaal2     MIPSGGTFKD  VITEGDGRTK  Y*.
Bnaal2     LIPSGGTFKD  IIV*......  ...
Consensus  MIPSGGAFKD  VITEGDGRTV  Y--
```

FIG. 5h

Pac751 - maize als2 AHAS isozyme as expressed from the pAC751 E. coli expression vector (same as figure 1)
Maizeals2 - maize als2 AHAS isozyme (plant)
Maizeals1 - maize als1 AHAS isozyme (plant)
Tobac1 - tobacco AHAS SuRA isozyme (plant)
Tobac2 - tobacco AHAS SuRB isozyme (plant)
Athcsr12 - Arabidopsis thaliana Csr 1.2 AHAS gene (plant)
Bnaal3 - Brassica napus AHAS III isozyme (plant)
Bnaal2 - Brassica napus AHAS II isozyme (plant)

STRUCTURE-BASED DESIGNED HERBICIDE RESISTANT PRODUCTS

This application is a 371 of PCT/US96/05782 filed Apr. 19, 1996, which is a continuation-in-part of U.S. Ser. No. 08/455,355 filed on May 31, 1995 issued as U.S. Pat. No. 5,928,937, which is a Division of Ser. No. 08/426,125 filed Apr. 20, 1995, issued as U.S. Pat. No. 5,853,973.

FIELD OF THE INVENTION

This invention pertains to structure-based modelling and design of variants of acetohydroxy acid synthase (AHAS) that are resistant to imidazolinones and other herbicides, the AHAS inhibiting herbicides, AHAS variants themselves, DNA encoding these variants, plants expressing these variants, and methods of weed management.

BACKGROUND OF THE INVENTION

Acetohydroxy acid synthase (AHAS) is an enzyme that catalyzes the initial step in the biosynthesis of isoleucine, leucine, and valine in bacteria, yeast, and plants. For example, the mature AHAS from *Zea mays* is approximately a 599-amino acid protein that is localized in the chloroplast (see FIG. 1; SEQ ID NO:1). The enzyme utilizes thiamine pyrophosphate (TPP) and flavin adenine dinucleotide (FAD) as cofactors and pyruvate as a substrate to form acetolactate. The enzyme also catalyzes the condensation of pyruvate and 2-ketobutyrate to form acetohydroxybutyrate. AHAS is also known as acetolactate synthase or acetolactate pyruvate lyase (carboxylating), and is designated EC 4.1.3.18. The active enzyme is probably at least a homodimer. Ibdah et al. (*Protein Science*, 3:479-S, 1994), in an abstract, disclose one model for the active site of AHAS.

A variety of herbicides including imidazolinone compounds such as imazethapyr (PURSUIT®—American Cyanamid Company-Wayne, N.J.), sulfonylurea-based compounds such as sulfometuron methyl (OUST®—E.I. du Pont de Nemours and Company-Wilmington, Del.), triazolopyrimidine sulfonamides (Broadstrike™—Dow Elanco; see Gerwick, et al., *Pestic. Sci.* 29:357–364, 1990), sulfamoylureas (Rodaway et al., *Mechanisms of Selectivity of Ac 322,140 in Paddy Rice, Wheat and Barley*, Proceedings of the Brighton Crop Protection Conference-Weeds, 1993), pyrimidyl-oxy-benzoic acids (STABLE®—Kumiai Chemical Industry Company, E.I. du Pont de Nemours and Company; see, The Pesticide Manual 10th Ed. pp. 888–889, Clive Tomlin, Ed., British Crop Protection Council, 49 Downing Street, Farmham, Surrey G49 7PH, UNITED KINGDOM), and sulfonylcarboxamides (Alvarado et al., U.S. Pat. No. 4,883,914) act by inhibiting AHAS enzymatic activity. (See, Chaleff et al., *Science* 224:1443, 1984; LaRossa et al., *J.Biol.Chem.* 259:8753, 1984; Ray, *Plant Physiol.* 75:827, 11984; Shaner et al., *Plant Physiol.* 76:545, 1984). These herbicides are highly effective and environmentally benign. Their use in agriculture, however, is limited by their lack of selectivity, since crops as well as undesirable weeds are sensitive to the phytotoxic effects of these herbicides.

Bedbrook et al., U.S. Pat. Nos. 5,013,659, 5,141,870, and 5,378,824, disclose several sulfonylurea resistant AHAS variants. However, these variants were either obtained by mutagenizing plants, seeds, or cells and selecting for herbicide-resistant mutants, or were derived from such mutants. This approach is unpredictable in that it relies (at least initially) on the random chance introduction of a relevant mutation, rather than a rational design approach based on a structural model of the target protein.

Thus, there is still a need in the art for methods and compositions that provide selective wide spectrum and/or specific herbicide resistance in cultivated crops. The present inventors have discovered that selective herbicide resistant variant forms of AHAS and plants containing the same can be prepared by structure-based modelling of AHAS against pyruvate oxidase (POX), identifying an herbicide binding pocket or pockets on the AHAS model, and designing specific mutations that alter the affinity of the herbicide for the binding pocket. These variants and plants are not inhibited or killed by one or more classes of herbicides and retain sufficient AHAS enzymatic activity to support crop growth.

BRIEF DESCRIPTION OF THE DRAWINGS

FIGS. 1A and 1B are illustrations of a 600 amino acid sequence corresponding to the approximately 599 amino acid sequence of acetohydroxy acid synthase (AHAS) from *Zea mays* (SEQ ID NO:1) which is given as an example of a plant AHAS enzyme. The sequence does not include a transit sequence, and the extra glycine is vestigial from a thrombin cleavage site. Residues Met53, Arg128, and Phe135 are shown in bold.

FIGS. 2A and 2B are an illustration of the alignment of the sequence of maize AHAS and pyruvate oxidase (POX) from *Lactobacillus planarum* (SEQ ID NO:2).

FIGS. 5A–5H are illustrations of the homology among AHAS amino acid sequences derived from different plant species. pAC 751 is maize als 2 AHAS isozyme as expressed from the pAC 751 *E. coil* expression vector as in FIG. 1 (SEQ ID NO:1); Maize als 2 is the maize als 2 AHAS isozyme (SEQ ID NO:3); Maize. als 1 is the maize als 1 AHAS isozyme (SEQ ID NO:4); Tobac 1 is the tobacco AHAS SuRA isozyme (SEQ ID NO:5); Tobac 2 is the tobacco AHAS SuRB isozyme (SEQ ID NO:6); Athcsr 12 is the *Arabidopsis thaliana* Csr 1.2 AHAS gene (SEQ ID NO:7); Bnaal 3 is the *Brassica napus* AHAS III isozyme (SEQ ID NO:8); and Bnaal 2 is the *Brassica napus* AHAS II isozyme (SEQ ID NO:9).

SUMMARY OF THE INVENTION

Figure 3A:
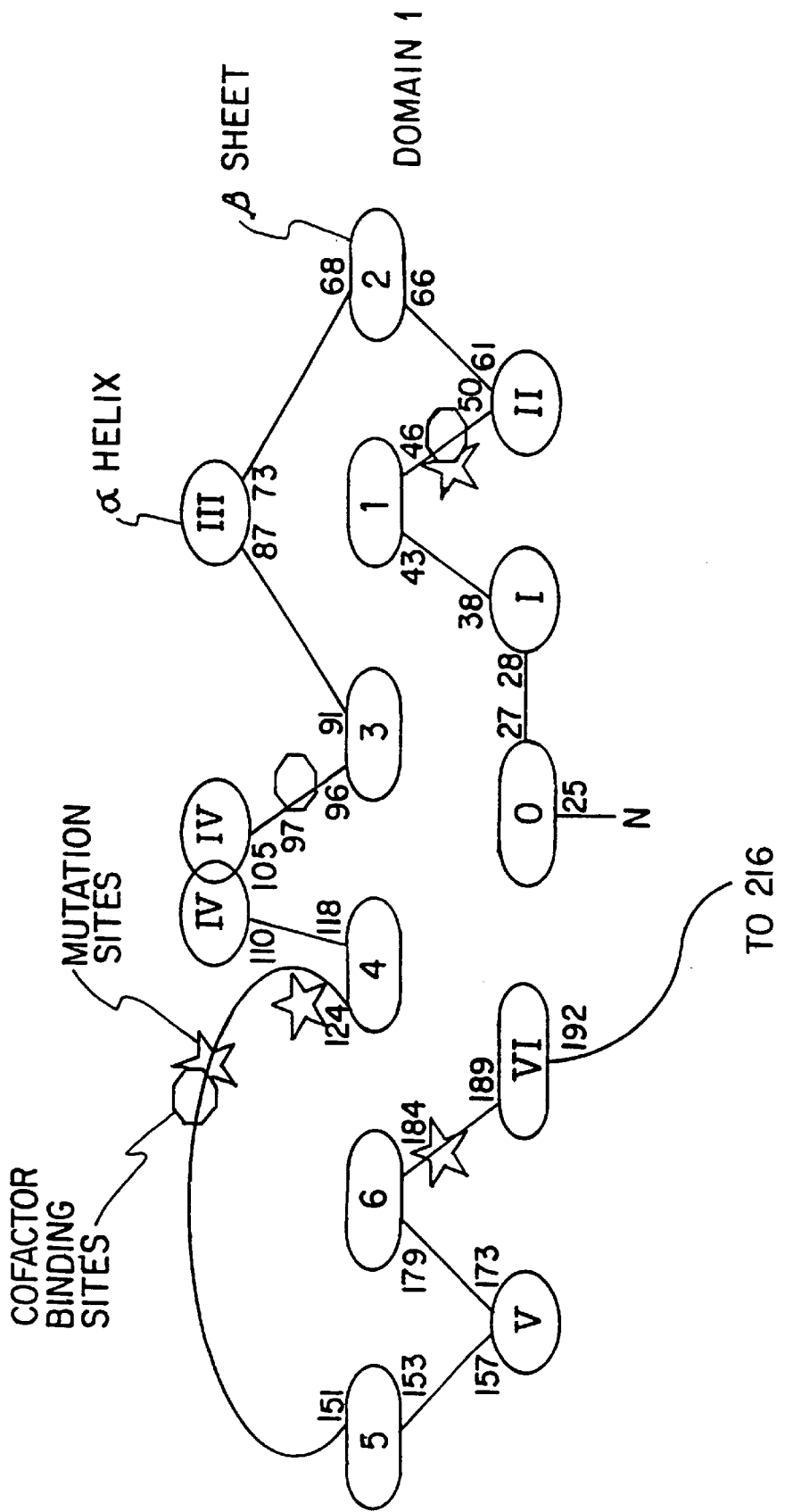
FIGS. 3A–3C are schematic representations of the secondary structure of an AHAS subunit. Regular secondary structure elements, α-helices and β-sheets, are depicted as circles and ellipses, respectively, and are numbered separately for each of the three domains within a subunit. Loops and coiled regions are represented by black lines, with numbers representing the approximate beginnings and ends of the elements. The locations of cofactor binding sites and known mutation sites are indicated by octahedrons and stars, respectively.
Figure 3B:
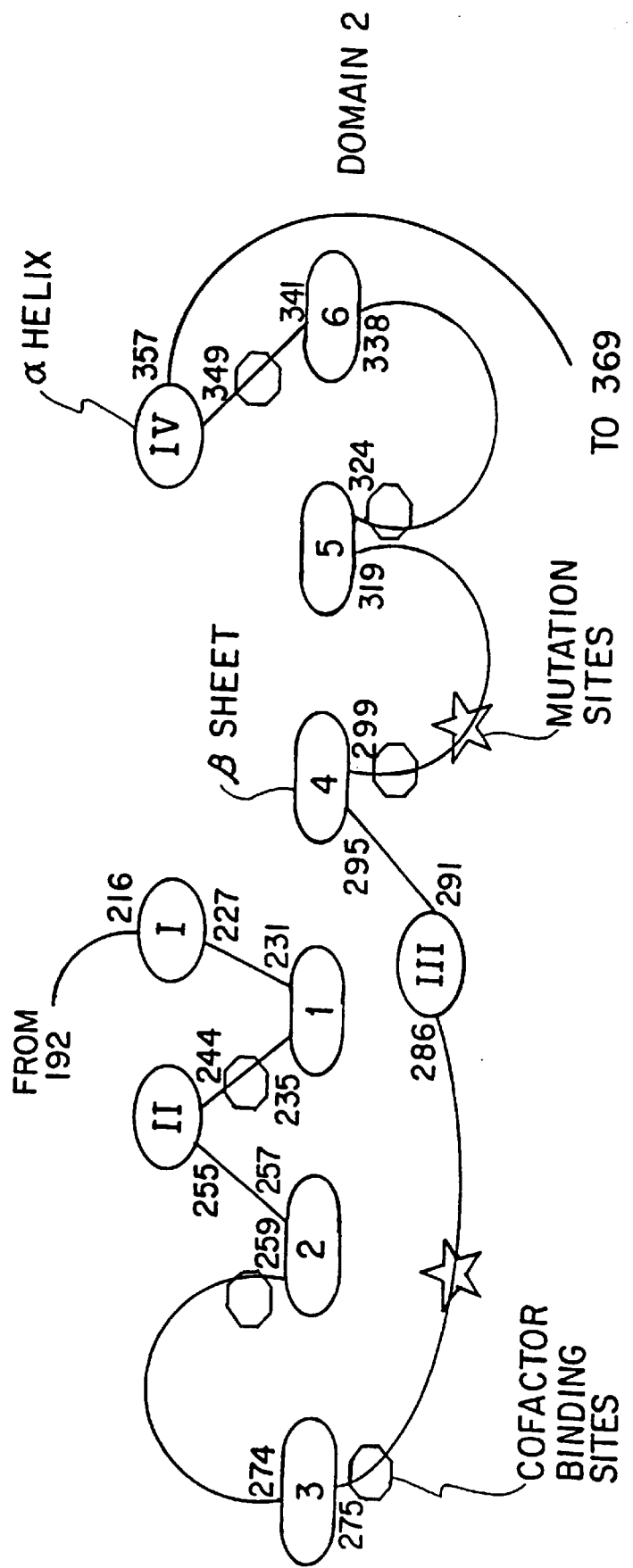
Figure 3C:
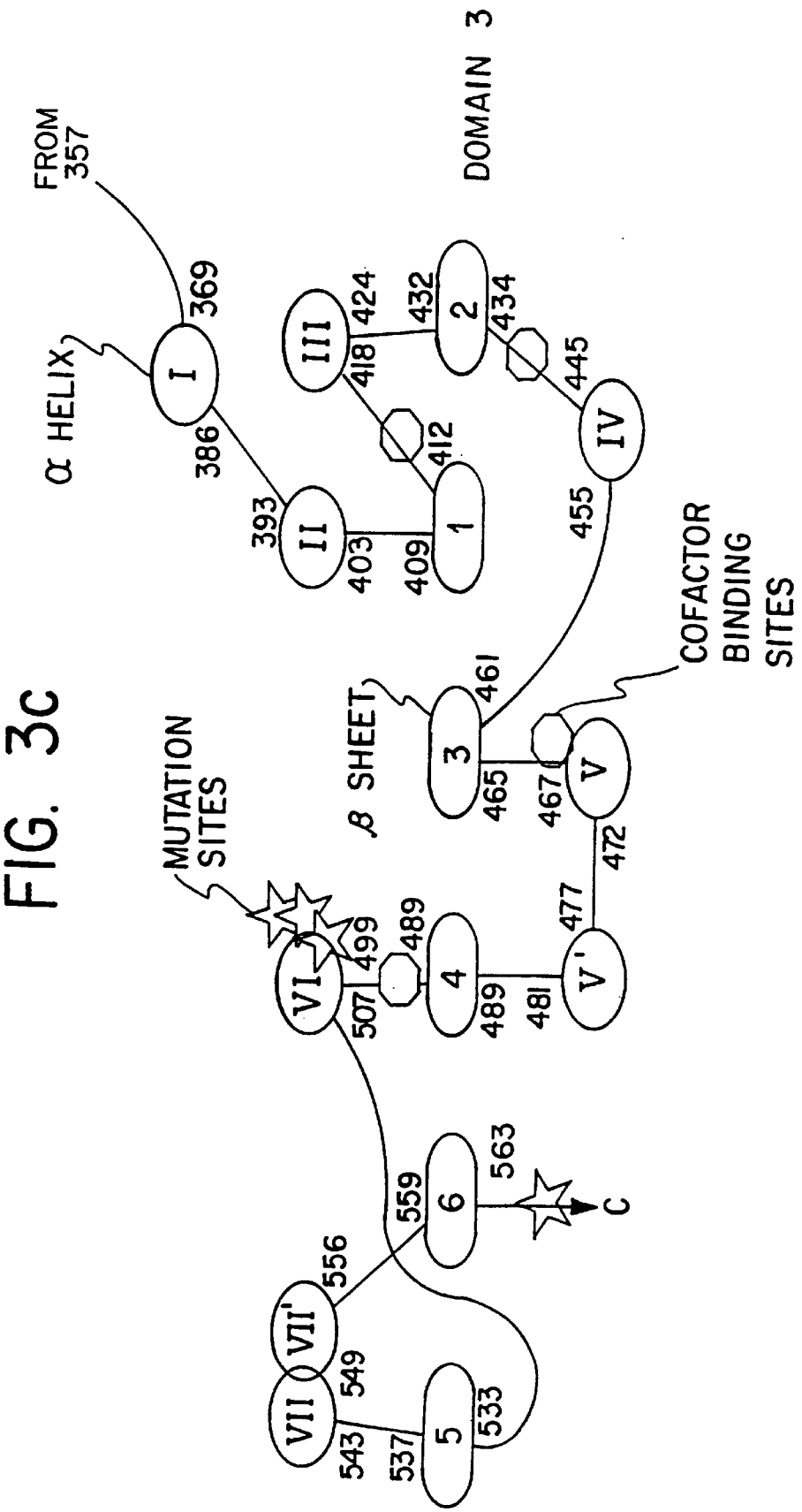
Figure 4:
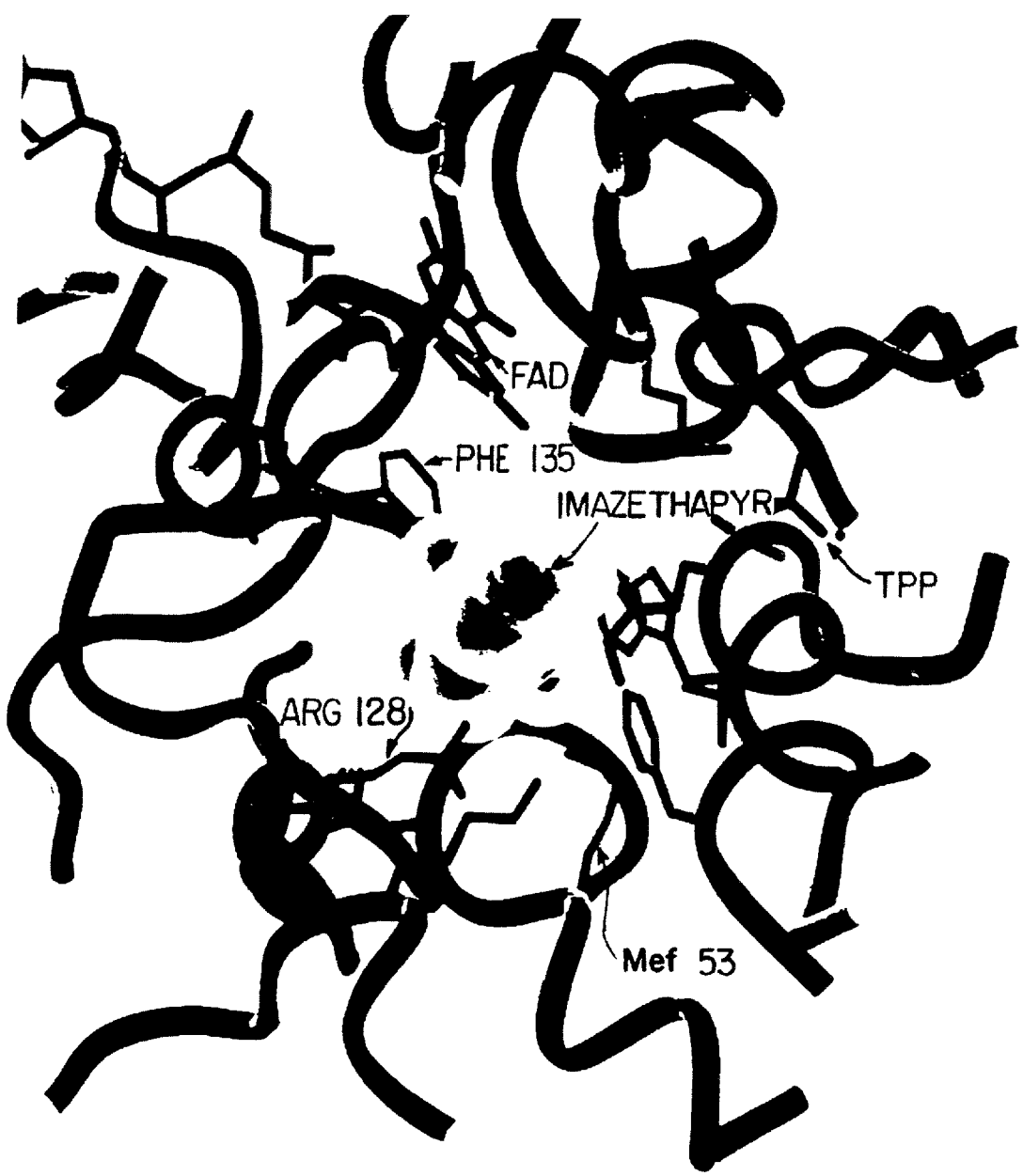
FIG. 4 is an illustration of a computer-generated model of the active site of maize AHAS with imazethapyr (PURSUIT® herbicide) modeled into the binding pocket.

The present invention provides a structure-based modelling method for the production of herbicide resistant AHAS variant protein. The method includes:

(a) aligning a target AHAS protein on pyruvate oxidase template or an AHAS modelling equivalent thereof to derive the three-dimensional structure of the target AHAS protein;

(b) modelling one or more herbicides into the three-dimensional structure to localize an herbicide binding pocket in the target AHAS protein;

(c) selecting as a target for a mutation, at least one amino acid position in the target AHAS protein, wherein the mutation alters the affinity of at least one herbicide for the binding pocket;

(d) mutating DNA encoding the target AHAS protein to produce a mutated DNA encoding a variant AHAS containing the mutation, such as, for example, at least one different amino acid, at the position; and (e) expressing the mutated DNA in a first cell, under conditions in which the variant AHAS containing the mutation, such as, for example, the different amino acid(s), at the position is produced.

The method further may include:

(f) expressing DNA encoding wild-type AHAS protein parallel in a second cell;

(g) purifying the wild-type and the variant AHAS proteins from the cells;

(h) assaying the wild-type and the variant AHAS proteins for catalytic activity in conversion of pyruvate to acetolactate or in the condensation of pyruvate and 2-ketobutyrate to form acetohydroxybutyrate, in the absence and in the presence of the herbicide; and (i) repeating steps (c)–(h), wherein the DNA encoding the AHAS variant of step (e) is used as the AHAS-encoding DNA in step (c) until a first herbicide resistant AHAS variant protein is identified having:

(i) in the absence of the at least one herbicide, (a) catalytic activity alone sufficient to maintain the viability of a cell in which it is expressed; or (b) catalytic activity in combination with any herbicide resistant AHAS variant protein also expressed in the cell, which may be the same as or different than the first AHAS variant protein, sufficient to maintain the viability of a cell in which it is expressed;

wherein the cell requires AHAS activity for viability; and (ii) catalytic activity that is more resistant to the at least one herbicide than is wild-type AHAS.

An alternate structure-based modelling method for the production of herbicide resistant AHAS variant protein is also provided. This method includes:

(a) aligning a target AHAS protein on a first AHAS template derived from a polypeptide having the sequence of FIG. 1 or a functional equivalent thereof to derive the three-dimensional structure of the target AHAS protein;

(b) modelling one or more herbicides into the three-dimensional structure to localize an herbicide binding pocket in the target AHAS protein;

(c) selecting as a target for a mutation, at least one amino acid position in the target AHAS protein, wherein the mutation alters the affinity of at least one herbicide for the binding pocket;

(d) mutating DNA encoding the target AHAS protein to produce a mutated DNA encoding a variant AHAS containing the mutation at the position; and (e) expressing the mutated DNA in a first cell, under conditions in which the variant AHAS containing the mutation at the position is produced.

This method can further include:

(f) expressing DNA encoding wild-type AHAS protein in parallel in a second cell;

(g) purifying the wild-type and the variant AHAS protein from the cells;

(h) assaying the wild-type and the variant AHAS protein for catalytic activity in conversion of pyruvate to acetolactate or in the condensation of pyruvate and 2-ketobutyrate to form acetohydroxybutyrate, in the absence and in the presence of the herbicide; and (i) repeating steps (c)–(h), wherein the DNA encoding the AHAS variant of step (e) is used as the AHAS-encoding DNA in step (c) until a first herbicide resistant AHAS variant protein is identified having:
  (i) in the absence of the at least one herbicide,
    (a) catalytic activity alone sufficient to maintain the viability of a cell in which it is expressed; or
    (b) catalytic activity in combination with any herbicide resistant AHAS variant protein also expressed in the cell, which may be the same as or different than the first AHAS variant protein, sufficient to maintain the viability of a cell in which it is expressed;
      wherein the cell requires AHAS activity for viability; and
  (ii) catalytic activity that is more resistant to the at least one herbicide than is wild-type AHAS.

In another alternate embodiment, the method includes:

(a) aligning a target AHAS protein on a first AHAS template having an identified herbicide binding pocket and having the sequence of FIG. 1 or a functional equivalent thereof to derive the three-dimensional structure of the target AHAS protein;

(b) selecting as a target for a mutation, at least one amino acid position in the target AHAS protein, wherein the mutation alters the affinity of at least one herbicide for the binding pocket;

(c) mutating DNA encoding the target AHAS protein to produce a mutated DNA encoding a variant AHAS containing the mutation at the position; and (d) expressing the mutated DNA in a first cell, under conditions in which the variant AHAS containing the mutation at the position is produced.

This method can further include:

(e) expressing DNA encoding wild-type target AHAS protein in parallel in a second cell;

(f) purifying the wild-type and the variant AHAS protein from the cells;

(g) assaying the wild-type and the variant AHAS protein for catalytic activity in conversion of pyruvate to acetolactate or in the condensation of pyruvate and 2-ketobutyrate to form acetohydroxybutyrate, in the absence and in the presence of the herbicide; and (h) repeating steps (b)–(g), wherein the DNA encoding the AHAS variant of step (d) is used as the AHAS-encoding DNA in step (b) until a first herbicide resistant AHAS variant protein is identified having:
  (i) in the absence of the at least one herbicide,
    (a) catalytic activity alone sufficient to maintain the viability of a cell in which it is expressed; or
    (b) catalytic activity in combination with any herbicide resistant AHAS variant protein also expressed in the cell, which may be the same as or different than the first AHAS variant protein, sufficient to maintain the viability of a cell in which it is expressed;
      wherein the cell requires AHAS activity for viability; and
  (ii) catalytic activity that is more resistant to the at least one herbicide than is wild-type AHAS.

In preferred embodiments of the above methods, the catalytic activity in the absence of the herbicide is at least about 5% and most preferably is more than about 20% of the catalytic activity of the wild-type AHAS. Where the herbicide is an imidazolinone herbicide, the herbicide resistant AHAS variant protein preferably has:

(i) catalytic activity in the absence of the herbicide of more than about 20% of the catalytic activity of the wild-type AHAS;
  (ii) catalytic activity that is relatively more resistant to the presence of imidazolinone herbicides compared to wild-type AHAS; and
  (iii) catalytic activity that is relatively more sensitive to the presence of sulfonylurea herbicides compared to imidazolinone herbicides.

The present invention further provides isolated DNA encoding acetohydroxy acid synthase (AHAS) variant proteins, the variant proteins comprising an AHAS protein modified by:

(i) substitution of at least one different amino acid residue at an amino acid residue of the sequence of FIG. 1 (SEQ ID NO:1) selected from the group consisting of P48, G49, S52, M53, E54, A84, A95, T96, S97, G98, P99, G100, A101, V125, R127, R128, M129, I130, G131, T132, D133, F135, Q136, D186, I187, T259, T260, L261, M262, G263, R276, M277, L278, G279, H281, G282, T283, V284, G300, V301, R302, F303, D304, R306, V307, T308, G309, K310, I311, E312, A313, F314, A315, S316, R317, A318, K319, I320, E329, I330, K332, N333, K334, Q335, T404, G413, V414, G415, Q416, H417, Q418, M419, W420, A421, A422, L434, S435, S436, A437, G438, L439, G440, A441, M442, G443, D467, G468, S469, L471, N473, L477, M479, Q495, H496, L497, G498, M499, V501, Q502, Q504, D505, R506, Y508, K509, A510, N511, R512, A513, H514, T515, S524, H572, Q573, E574, H575, V576, L577, P578, M579, I580, P581, G583, G584, functional equivalents of any of the foregoing, and any combination of any of the foregoing;

(ii) deletion of up to 5 amino acid residues preceding, or up to 5 amino acid residues following at least one amino acid residue of the sequence of FIG. 1 (SEQ ID NO:1) selected from the group consisting of P48, G49, S52, M53, E54, A84, A95, T96, S97, G98, P99, G100, A101, V125, R127, R128, M129, I130, G131, T132, D133, F135, Q136, D186, I187, T259, T260, L261, M262, G263, R276, M277, L278, G279, H281, G282, T283, V284, G300, V301, R302, F303, D304, R306, V307, T308, G309, K310, I311, E312, A313, F314, A315, S316, R317, A318, K319, I320, E329, I330, K332, N333, K334, Q335, T404, G413, V414, G415, Q416, H417, Q418, M419, W420, A421, A422, L434, S435, S436, A437, G438, L439, G440, A441, M442, G443, D467, G468, S469, L471, N473, L477, M479, Q495, H496, L497, G498, M499, V501, Q502, Q504, D505, R506, Y508, K509, A510, N511, R512, A513, H514, T515, S524, H572, Q573, E574, H575, V576, L577, P578, M579, I580, P581, G583, G584, functional equivalents of any of the foregoing, and any combination of any of the foregoing;

(iii) deletion of at least one amino acid residue or a functional equivalent thereof between Q124 and H150 of the sequence of FIG. 1 (SEQ ID NO:1);

(iv) addition of at least one amino acid residue or a functional equivalent thereof between Q124 and H150 of the sequence of FIG. 1 (SEQ ID NO:1);

(v) deletion of at least one amino acid residue or a functional equivalent thereof between G300 and D324 of the sequence of FIG. 1 (SEQ ID NO:1);

(vi) addition of at least one amino acid residue or a functional equivalent thereof between G300 and D324 of the sequence of FIG. 1 (SEQ ID NO:1); or (vii) any combination of any of the foregoing.

In this numbering system, residue #2 corresponds to the putative amino terminus of the mature protein, i.e., after removal of a chloroplast targeting peptide.

The above modifications are directed to altering the ability of an herbicide, and preferably an imidazolinone-based herbicide, to inhibit the enzymatic activity of the protein. In a preferred embodiment, the isolated DNA encodes an herbicide-resistant variant of AHAS. Also provided are DNA vectors comprising DNA encoding these AHAS variants, variant AHAS proteins themselves, and cells, grown either in vivo or in cell culture, that express the AHAS variants or comprise these vectors.

In another aspect, the present invention provides a method for conferring herbicide resistance on a cell or cells and particularly a plant cell or cells such as, for example, a seed. An AHAS gene, preferably the *Arabidopsis thaliana* AHAS gene, is mutated to alter the ability of an herbicide to inhibit the enzymatic activity of the AHAS. The mutant gene is cloned into a compatible expression vector, and the gene is transformed into an herbicide-sensitive cell under conditions in which it is expressed at sufficient levels to confer herbicide resistance on the cell.

Also contemplated are methods for weed control, wherein a crop containing an herbicide resistant AHAS gene according to the present invention is cultivated and treated with a weed-controlling effective amount of the herbicide.

Also disclosed is a structure-based modelling method for the preparation of a first herbicide which inhibits AHAS activity. The method comprises:

(a) aligning a target AHAS protein on pyruvate oxidase template or an AHAS modelling functional equivalent thereof to derive the three-dimensional structure of the target AHAS protein;

(b) modelling a second herbicide having AHAS inhibiting activity into the three-dimensional structure to derive the location, structure, or a combination thereof of an herbicide binding pocket in the target AHAS protein; and (c) designing a non-peptidic first herbicide which will interact with, and preferably will bind to, an AHAS activity inhibiting effective portion of the binding pocket, wherein the first herbicide inhibits the AHAS activity sufficiently to destroy the viability of a cell which requires AHAS activity for viability.

An alternative structure-based modelling method for the production of a first herbicide which inhibits AHAS activity, is also enclosed. The method comprises:

(a) aligning a target AHAS protein on a first AHAS template derived from a polypeptide having the sequence of FIG. 1 or a functional equivalent thereof, to derive the three-dimensional structure of the target AHAS protein;

(b) modelling a second herbicide having AHAS inhibiting activity into the three-dimensional structure to derive the location, structure, or a combination thereof of an herbicide binding pocket in the target AHAS protein; and (c) designing a non-peptidic first herbicide which will interact with, and preferably will bind to, an AHAS activity inhibiting effective portion of the binding pocket, wherein the first herbicide inhibits the AHAS activity sufficiently to destroy the viability of a cell which requires AHAS activity for viability.

Preferably in each method, the first herbicide contains at least one functional group that interacts with a functional group of the binding pocket.

DETAILED DESCRIPTION OF THE INVENTION

The present invention encompasses the rational design or structure-based molecular modelling of modified versions of the enzyme AHAS and AHAS inhibiting herbicides. These modified enzymes (AHAS variant proteins) are resistant to the action of herbicides. The present invention also encompasses DNAs that encode these variants, vectors that include these DNAs, the AHAS variant proteins, and cells that express these variants. Additionally provided are methods for producing herbicide resistance in plants by expressing these variants and methods of weed control. The DNA and the AHAS variants of the present invention were discovered in studies that were based on molecular modelling of the structure of AHAS.

Rational Structure-Based Design of AHAS Variants and AHAS Inhibiting Herbicides Herbicide-resistant variants of AHAS according to the present invention are useful in conferring herbicide resistance in plants and can be designed with the POX model, AHAS model, or functional equivalents thereof, such as, for example, transketolases, carboligases, pyruvate decarboxylase, proteins that bind FAD and/or TPP as a cofactor, or any proteins which have structural features similar to POX and/or AHAS; with an AHAS model such as a model having the sequence of FIG. 1 (SEQ ID NO:1); or with a functional equivalent of the sequence of FIG. 1 (SEQ ID NO:1) including a variant modeled from a previous model. Proteins that can be used include any proteins having less than a root mean square deviation of less than 3.5 angstroms in their Cα carbons relative to any of the above-listed molecules. AHAS directed herbicides can be similarly modelled from these templates. A functional equivalent of an AHAS amino acid sequence is a sequence having substantial, i.e., 60–70%, homology, particularly in conserved regions such as, for example, a putative binding pocket. The degree of homology can be determined by simple alignment based on programs known in the art, such as, for example, GAP and PILEUP by GCG. Homology means identical amino acids or conservative substitutions. A functional equivalent of a particular amino acid residue in the AHAS protein of FIG. 1 (SEQ ID NO:1) is an amino acid residue of another AHAS protein which when aligned with the sequence of FIG. 1 (SEQ ID NO:1) by programs known in the art, such as, for example, GAP and PILEUP by GCG, is in the same position as the amino acid residue of FIG. 1 (SEQ ID NO:1).

Rational design steps typically include: (1) alignment of a target AHAS protein with a POX backbone or structure or an AHAS backbone or structure; (2) optionally, and if the AHAS backbone has an identified herbicide binding pocket, modelling one or more herbicides into the three-dimensional structure to localize an herbicide binding pocket in the target protein; (3) selection of a mutation based upon the model; (4) site-directed mutagenesis; and (5) expression and purification of the variants. Additional steps can include (6) assaying of enzymatic properties and (7) evaluation of suitable variants by comparison to the properties of the wild-type AHAS. Each step is discussed separately below.

1. Molecular Modelling

Molecular modelling (and particularly protein homology modelling) techniques can provide an understanding of the structure and activity of a given protein. The structural model of a protein can be determined directly from experimental data such as x-ray crystallography, indirectly by homology modelling or the like, or combinations thereof (See White, et al., *Annu. Rev. Biophys. Biomol. Struct.,* 23:349, 1994). Elucidation of the three-dimensional structure of AHAS provides a basis for the development of a rational scheme for mutation of particular amino acid residues within AHAS that confer herbicide resistance on the polypeptide.

Molecular modelling of the structure of *Zea mays* AHAS, using as a template the known X-ray crystal structure of related pyruvate oxidase (POX) from *Lactobacillus plantarum,* provides a three-dimensional model of AHAS structure that is useful for the design of herbicide-resistant AHAS variants or AHAS inhibiting herbicides. This modelling procedure takes advantage of the fact that AHAS and POX share a number of biochemical characteristics and may be derived from a common ancestral gene (Chang et al., *J.Bacteriol.* 170:3937, 1988).

Because of the high degree of cross-species homology in AHAS the modelled AHAS described herein or functional equivalents thereof can also be used as templates for AHAS variant protein design.

Derivation of one model using interactive molecular graphics and alignments is described in detail below. The three-dimensional AHAS structure that results from this procedure predicts the approximate spatial organization of the active site of the enzyme and of the binding site or pocket of inhibitors such as herbicides including, but not limited to, imidazolinone herbicides. The model is then refined and re-interpreted based on biochemical studies which are also described below.

Protein homology modelling requires the alignment of the primary sequence of the protein under study with a second protein whose crystal structure is known. Pyruvate oxidase (POX) was chosen for AHAS homology modelling because POX and AHAS share a number of biochemical characteristics. For example, both AHAS and POX share aspects of enzymatic reaction mechanisms, as well as cofactor and metal requirements. In both enzymes thiamine pyrophosphate (TPP), flavin adenine dinucleotide (FAD), and a divalent cation are required for enzymatic activity. FAD mediates a redox reaction during catalysis in POX but presumably has only a structural function in AHAS, which is possibly a vestigial remnant from the evolution of AHAS from POX. Both enzymes utilize pyruvate as a substrate and form hydroxyethyl thiamine pyrophosphate as a stable reaction intermediate (Schloss, J. V. et al. In *Biosynthesis of branched chain amino acids,* Barak, Z. J. M., Chipman, D. M., Schloss, J. V. (eds) VCH Publishers, Weinheim, Germany, 1990).

Additionally, AHAS activity is present in chimeric POX-AHAS proteins consisting of the N-terminal half of POX and the C-terminal half of AHAS, and there is a small degree of AHAS activity exhibited by POX itself. AHAS and POX also exhibit similar properties in solution (Risse, B. et al, *Protein Sci.* 1: 1699 and 1710, 1992; Singh, B. K., & Schmitt, G. K. (1989), *FEBS Letters,* 2: 113; Singh, B. K. et al. (1989) In: *Prospects for Amino Acid Biosynthesis Inhibitors in Crop Protection and Pharmaceutical Chemistry,* (Lopping, L. G., et al., eds., BCPC Monograph p. 87). With increasing protein concentration, both POX and AHAS undergo stepwise transitions from monomers to dimers and tetramers. Increases in FAD concentration also induce higher orders of subunit assembly. The tetrameric form of both proteins is most stable to heat and chemical denaturation.

Furthermore, the crystal structure of POX from *Lactobacillus planarum* had been solved by Muller et al., *Science* 259:965, 1993. The present inventors found that based in part upon the degree of physical, biochemical, and genetic homology between AHAS and POX, the X-ray crystal structure of POX could be used as a structural starting point for homology modelling of the AHAS structure.

AHAS and *L. plantarum* POX sequences were not similar enough for a completely computerized alignment, however. Overall, only about 20% of the amino acids are identical, while about 50% of the residues are of similar class (i.e. acidic, basic, aromatic, and the like). However, if the sequences are compared with respect to hydrophilic and hydrophobic residue classifications, over 500 of the 600 amino acids match. Secondary structure predictions for AHAS (Holley et al., *Proc.Natl.Acad.Sci.USA* 86:152, 1989) revealed a strong similarity to the actual secondary structure of POX. For nearly 70% of the residues, the predicted AHAS secondary structure matches that of POX.

POX monomers consist of three domains, all having a central, parallel β-sheet with crossovers consisting of α-helices and long loops. (Muller et al., *Science* 259:965, 1993). The topology of the sheets differs between the domains, i.e. in the first and third domains, the strands are assembled to the β-sheet in the sequence 2-1-3-4-6-5, while in the β-sheet of the second domain, the sequence reads 3-2-1-4-5-6.

Computer generated alignments were based on secondary structure prediction and sequence homology. The conventional pair-wise sequence alignment method described by Needleman and Wunch, *J. Mol. Biol,* 48: 443, 1970, was used. Two sequences were aligned to maximize the alignment score. The alignment score (homology score) is the sum of the scores for all pairs of aligned residues, plus an optional penalty for the introduction of gaps into the alignment. The score for the alignment of a pair of residues is a tabulated integer value. The homology scoring system is based on observing the frequency of divergence between a given pair of residues. (MO Dayhoff, RM Schwartz & BC Orcutt "Atlas of Protein Sequence and Structure" vol. 5 suppl. 3 pp. 345–362, 1978).

The alignments were further refined by repositioning gaps so as to conserve continuous regular secondary structures. Amino acid substitutions generated by evaluation of likely alignment schemes were compared by means of interactive molecular graphics. Alignments with the most conservative substitutions with respect to the particular functionality of the amino acids within a given site were chosen. The final alignment of both POX and AHAS is displayed in FIG. 2. Conserved clusters of residues were identified, in particular for the TPP binding site and for parts of the FAD binding site. The alignment revealed a high similarity between AHAS and POX for the first domain, for most parts of the second domain, and for about half of the third domain. Most of the regions that aligned poorly and may fold differently in POX and in AHAS were expected to be at the surface of the protein and were not involved in cofactor or inhibitor binding. The prediction of mutation sites is not substantially affected by small shifts in the alignment.

Most TPP binding residues are highly conserved between POX and AHAS (e.g. P48-G49-G50). In some cases, residues that were close to TPP differ between POX and AHAS but remain within a region that is highly conserved (for example, residues 90–110). On the other hand, the FAD binding site appeared to be less conserved. Although some FAD binding residues were strongly conserved (for example, D325-I326-D327-P328), others clearly differed between AHAS and POX (for example, residues in the loop from positions 278 to 285 are not homologous. A detailed analysis revealed that, at least for some of the less-conserved contact sites, the interactions were mediated by the polypeptide backbone rather than by the side chains. Hence, conservation was only required for the polypeptide fold and was not required for the amino acid sequence (for example, the backbone of residues 258–263 binds the ribitol chain of FAD). One half of the adenine and the isoalloxazine binding sites clearly differ.

After aligning the primary structure, a homology model was built by transposition of AHAS amino acid sequences to the POX template structure. Missing coordinates were built stepwise using templates of amino acid residues to complete undefined side chains. Data bank searches and energy minimization of small parts of the molecule were used to complete the conformations of undefined loop regions. The cofactors TPP and FAD were modeled into their binding pockets. This model was then subjected to a complete, 5000 cycle energy minimization. All computer modelling was performed in an IRIS Indigo Elan R4000 Workstation from Silicon Graphics Co. Interactive molecular modelling and energy-minimization were performed using Quanta/CHARMm 4.0 from Molecular Simulations Inc. During this step, the conformation was stable, indicating that no strongly disfavored interactions, such as, for example, close van der Waals contacts, had occurred. The results are shown schematically in FIG. 3.

Characteristics of Predicted AHAS Structure

Inspection of the modelled AHAS structure described above revealed that most of the protein folds with a backbone that is energetically reasonable, with most hydrophilic side chains accessible to the solvent. The surface of the β-sheets are smooth and accommodate the cross-over regions that are attached to them.

A model for dimeric AHAS was generated by duplicating the coordinates of the energy minimized monomeric AHAS and superimposing the two copies on two POX subunits using pairs of Cα coordinates as defined in the alignment scheme. The polypeptide chain of AHAS folds into three similarly folded domains composed of a six-stranded parallel β-sheet core surrounded by long "loops" and α-helices. Two subunits are assembled such that the first domain of one subunit is in close proximity to the cofactor-binding domains 2 and 3 of the other subunit. A solvent-filled space remains between the subunits at this site. This pocket, which is defined by the confluence of the three domains, is the proposed entry site for the substrate. It is also proposed to be the binding site for herbicides.

The inner surface of the binding pocket is outlined by the cofactors. The thiazol of TPP is positioned at the bottom of the pocket. Domain 3 contributes to the inner surface of the pocket with a short α-helix that points its axis towards the pyrophosphate of TPP, compensating the phosphate charges with its dipolar moment. This critical helix, which starts with G498, a "turn" residue in close contact with TPP, and which ends at F507, contains three known mutation sites for sulfonylurea resistance: V500, W503, and F507 (See, U.S. Pat. Nos. 5,013,659; 5,141,870; and 5,378,824). In domain 1, the loop defined as P48-S52 (between β-strand 2 and α-helix 2) faces W503, a mutation in which confers resistance to imidazolinones. Residues Y47 to G50 are also in contact with TPP. This loop is adjacent to P184-Q189, another turn, which connects the last strand of the β-sheet of domain 1 with a β-strand that connects with domain 2. Within the pocket, near its entrance, is a long region of domain 1 that interacts with a complementary stretch of domain 2. Residues 125–129 and 133–137 of domain 1 and residues 304–313 of domain 2 are at the surface of the pocket. A turn consisting of T96-G100 is between loop 125–129 and TPP. A further stretch of domain 3 and two regions of domain 2 that line the binding pocket are at the opposite corner of the pocket. Residues 572, 575, 582, and 583 of domain 3 define the pocket surface on one side. The remaining part of the interior of the pocket's surface is defined by FAD and by a loop, L278-G282, that contacts the isoalloxazine ring of FAD.

The structural models of the AHAS protein can also be used for the rational design of herbicides or AHAS inhibitors.

2. Modelling of Herbicides Into Binding Sites

Imazethapyr, the active imidazolinone in PURSUIT®, was positioned into its proposed binding site using interactive molecular graphics (FIG. 4) and the software described above (FIG. 4). K185 was chosen as an "anchor" to interact with the charge of the carboxyl group. The imidazolinone's NH—CO unit was placed to form hydrogen bonds to G50 and A51. This positioned the methyl substitute of imazethapyr close to V500 on the backbone of the small α-helix. The isopropyl group is possibly bound by hydrophobic residues of the amino acids in the region of residues 125–135 that contribute to the inner surface of the pocket. The pyridine ring is most probably "sandwiched" between A134 or F135, F507 and W503. W503 also interacts with the imidazolinone ring system.

In a similar fashion, the sulfonylurea herbicides were modelled into a site that partially overlapped the described imidazolinone binding site. Overlap of sulfonylurea and imidazolinone binding sites was consistent with competition binding experiments and with established mutant data, which show that the same mutation in maize, W503L, can confer resistance to both herbicides. In these models, most of the known mutation sites that confer sulfonylurea herbicide resistance, i.e. G50, A51, K185, V500, W503, F507, are in close contact to the bound herbicides. P126 and A51 are required for keeping the K185 side chain in place by generating a hydrophobic pore. S582, a site for specific imidazolinone resistance, is distant from the binding region and is located in the region where the homology is so poor that a change in the fold is expected. The FAD binding site apparently has low homology between AHAS and POX in this region; S582 is a residue that confers resistance in maize, and that S582 and its adjacent residues are in close contact to the active site pocket. It is proposed that FAD and the loop region encompassing residues 278 to 285 move slightly away from the third domain, (downward in FIG. 4) and that a loop that contains S582 folds into the space between the helix at positions 499 to 507 and the loop at positions 278 to 285. D305, another known resistance site, is close to FAD and modulates the interaction between domains 1 and 2. M280 may either be involved in positioning of the helix at positions 498 to 507 or directly in inhibitor binding. M280 and D305 could also be directly involved in inhibitor binding if domains 1 and 2 move slightly closer to each other.

3. Selection of Mutations

Specific amino acid residues are pinpointed as sites for the introduction of mutations into the primary sequence of AHAS. These amino acids are selected based upon their position in that if that amino acid residue position is modified, there will be a resultant alteration (i.e. decline) in the affinity of an herbicide for the binding pocket. It is not necessary that the mutation position reside in the binding pocket as amino acid residues outside the pocket itself can alter the pocket charge or configuration. The selection of target sites for mutation is achieved using molecular models as described above. For example according to the model above, arginine at position 128 (designated R128 in FIG. 1 using the single-letter code for amino acids) is located near the entrance to the substrate- and herbicide-binding pocket and has a large degree of conformational freedom that may allow it to participate in transport of charged herbicides into the binding pocket. Therefore, this residue is substituted by alanine to remove both its charge and its long hydrophobic side chain. (The resulting mutation is designated R128A).

The mutations may comprise simple substitutions, which replace the wild-type sequence with any other amino acid. Alternatively, the mutations may comprise deletions or additions of one or more amino acids, preferably up to 5, at a given site. The added sequence may comprise an amino acid sequence known to exist in another protein, or may comprise a completely synthetic sequence. Furthermore, more than one mutation and/or more than one type of mutation may be introduced into a single polypeptide.

4. Site-Directed Mutagenesis

The DNA encoding AHAS can be manipulated so as to introduce the desired mutations. Mutagenesis is carried out using methods that are standard in the art, as described in, for example, Higuchi, R., Recombinant PCR, In M. A. Innis, et al., eds, *PCR Protocols: A Guide to Methods and Applications,* Academic Press, pp. 177–183, 1990.

5. Expression and Purification of Variants

The mutated or variant AHAS sequence is cloned into a DNA expression vector (see, e.g., Example 3) and is expressed in a suitable cell such as, for example, *E. coli.* Preferably, the DNA encoding AHAS is linked to a transcription regulatory element, and the variant AHAS is expressed as part of a fusion protein, for example, glutathione-S-transferase, to facilitate purification (see Example 3 below). The variant AHAS is then purified using affinity chromatography or any other suitable method known in the art. "Purification" of an AHAS polypeptide refers to the isolation of the AHAS polypeptide in a form that allows its enzymatic activity to be measured without interference by other components of the cell in which the polypeptide is expressed.

6. Assaying of Enzymatic Properties

The purified variant AHAS may be assayed for one or more of the following three properties:

(a) specific or catalytic activity for conversion of pyruvate to acetolactate (expressed as units/mg pure AHAS, wherein a unit of activity is defined as 1 $\mu$mole acetolactate produced/hour), or for condensation of pyruvate and 2-ketobutyrate to form acetohydroxybutyrate (expressed as units/mg pure AHAS, wherein a unit of activity is defined as 1$\mu$ mole acetohydroxybutyrate produced/hr.;

(b) level of inhibition by herbicide, such as, for example, imidazolinone (expressed as $IC_{50}$, the concentration at which 50% of the activity of the enzyme is inhibited); and (c) selectivity of resistance to the selected herbicide vs. other herbicides. The selectivity index is defined as the fold resistance of the mutant to imidazolinones relative to the wild-type enzyme, divided by the fold resistance of the same mutant to other herbicides also relative to the wild-type). Fold resistance to an herbicide relative to the wild-type enzyme is expressed as the $IC_{50}$ of variant, divided by the $IC_{50}$ of the wild type. The selectivity index (S.I.) is thus represented by the following equation:

$$S.I. = \frac{IC_{50}\text{ of variant for herb.A}/IC_{50}\text{ of wild type for herb.A}}{IC_{50}\text{ of variant for herb.B}/IC_{50}\text{ of wild type for herb.B}}.$$

Suitable assay systems for making these determinations include, but are not limited to, those described in detail in Example 4 below.

7.a. Evaluation of Suitable Variants

The enzymatic properties of variant AHAS polypeptides are compared to the wild-type AHAS. Preferably, a given mutation results in an AHAS variant polypeptide that retains in vitro enzymatic activity towards pyruvate or pyruvate and 2-ketobutyrate, i.e., the conversion of pyruvate to acetolactate or in the condensation of pyruvate and 2-ketobutyrate to form acetohydroxybutyrate (and thus is expected to be biologically active in vivo), while exhibiting catalytic activity that is relatively more resistant to the selected herbicide (s) than is wild-type AHAS. Preferably, the variant AHAS exhibits:

(i) in the absence of the at least one herbicide, (a) catalytic activity alone sufficient to maintain the viability of a cell in which it is expressed; or (b) catalytic activity in combination with any herbicide resistant AHAS variant protein also expressed in the cell, which may be the same as or different than the first AHAS variant protein, sufficient to maintain the viability of a cell in which it is expressed;

wherein the cell requires AHAS activity for viability; and (ii) catalytic activity that is more resistant to the at least one herbicide than is wild type AHAS;

and that is relatively more resistant to the herbicide(s) than is wild-type AHAS.

Therefore, any one specific AHAS variant protein need not have the total catalytic activity necessary to maintain the viability of the cell, but must have some catalytic activity in an amount, alone or in combination with the catalytic activity of additional copies of the same AHAS variant and/or the catalytic activity of other AHAS variant protein (s), sufficient to maintain the viability of a cell that requires AHAS activity for viability. For example, catalytic activity may be increased to minimum acceptable levels by introducing multiple copies of a variant encoding gene into the cell or by introducing the gene which further includes a relatively strong promoter to enhance the production of the variant.

More resistant means that the catalytic activity of the variant is diminished by the herbicide(s), if at all, to a lesser degree than wild-type AHAS catalytic activity is diminished by the herbicide(s). Preferred more resistant variant AHAS retains sufficient catalytic to maintain the viability of a cell, plant, or organism wherein at the same concentration of the same herbicide(s), wild-type AHAS would not retain sufficient catalytic activity to maintain the viability of the cell, plant, or organism.

Preferably the catalytic activity in the absence of herbicide(s) is at least about 5% and, most preferably, is more than about 20% of the catalytic activity of the wild-type AHAS in the absence of herbicide(s). Most preferred AHAS variants are more resistant to imidazolinone herbicides than to other herbicides, such as sulfonylurea-based herbicides, though in some applications selectivity is neither needed nor preferred.

In the case of imidazolinone-resistant variant AHAS, it is preferred that the AHAS variant protein has (i) catalytic activity in the absence of said herbicide of more than about 20% of the catalytic activity of said wild-type AHAS;

(ii) catalytic activity that is relatively more resistant to presence of imidazolinone herbicides compared to wild type AHAS; and (iii) catalytic activity that is relatively more sensitive to the presence of sulfonylurea herbicides compared to imidazolinone herbicides. Most preferred herbicide-resistant AHAS variants exhibit a minimum specific activity of about 20 units/mg, minimal or no inhibition by imidazolinone, and a selectivity index ranging from about 1.3 to about 3000 relative to other herbicides.

Without wishing to be bound by theory, it is believed that systematic and iterative application of this method to wild type or other target AHAS protein will result in the production of AHAS variants having the desired properties of high enzymatic activity as explained above and resistance to one or more classes of herbicides. For example, mutation of a wild-type AHAS sequence at a particular position to a given amino acid may result in a mutant that exhibits a high degree of herbicide resistance but a significant loss of enzymatic activity towards pyruvate or pyruvate and 2-ketobutyrate. In a second application of the above method, the starting or target AHAS polypeptide would then be this variant (in place of the wild-type AHAS). Rational design then involves substituting other amino acids at the originally mutated position and/or adding or deleting amino acids at selected points or ranges in the expectation of retaining herbicide resistance but also maintaining a higher level of enzymatic activity.

The structure-based rational design of herbicide resistant AHAS proteins offers many advantages over conventional approaches that rely on random mutagenesis and selection. For example, when substitution of a particular amino acid with another requires substitution of more than one nucleotide within the codon, the likelihood of this occurring randomly is so low as to be impractical. By contrast, even double or triple changes in nucleotide sequence within a codon can be easily implemented when suggested by a rational design approach. For example, one rationally designed mutation to confer selective imidazolinone resistance requires a change from arginine to glutamate. Arginine is encoded by CGT, CGC, CGA, CGG, AGA, AGG, while glutamate is encoded by GAA and GAG. Since none of the arginine codons begins with GA, this mutation would require a double substitution of adjacent nucleotides which would occur so rarely using random mutagenesis as to be unpredictable and unrepeatable with any certainty of success. Although mutation frequency can be increased during random mutagenesis, alterations in nucleotide sequence would have an equal probability of occurring throughout the AHAS gene, in the absence of prior site-direction of the mutations. This increases the chance of obtaining an irrelevant mutation that interferes with enzymatic activity. Similarly, it would be rare, using random mutagenesis, to find a multiple amino acid substitution, deletion, or substitution/deletion mutation that confers herbicide resistance while maintaining catalytic activity. Deletion mutations that confer herbicide resistance would also be unlikely using a random mutagenesis approach. Deletions would need to be limited to small regions and would have to occur in triplets so as to retain the AHAS reading frame in order to retain enzymatic activity.

However, with a rational structure-based approach, double amino acid substitution and/or deletion mutations are relatively easily achieved and precisely targeted. Furthermore, different mutagens used in random mutagenesis create specific types of mutations. For example, sodium azide creates point substitution mutations in plants, while radiation tends to create deletions. Accordingly, two mutagenesis protocols would have to be employed to obtain a multiple combination substitution/deletion.

Finally, the present structure-based method for rational design of herbicide-resistant AHAS variants allows for iterative improvement of herbicide resistance mutations, a step that is not facilitated by random mutagenesis. Identification of a mutation site for herbicide resistance by random mutagenesis may offer little, if any, predictive value for guiding further improvements in the characteristics of the mutant. The present structure-based approach, on the other hand, allows improvements to be implemented based on the position, environment, and function of the amino acid position in the structural model.

The iterative improvement method also allows the independent manipulation of three important properties of AHAS: level of resistance, selectivity of resistance, and catalytic efficiency. For example, compensatory mutations can be designed in a predictive manner. If a particular mutation has a deleterious effect on the activity of an enzyme, a second compensatory mutation may be used to restore activity. For example, a change in the net charge within a domain when a charged residue is introduced or lost due to a mutation can be compensated by introducing a second mutation. Prediction of the position and type of residue(s) to introduce, delete, or substitute at the second site in order to restore enzymatic activity requires a knowledge of structure-function relationships derived from a model such as that described herein.

7.b. Design of Non-Peptide Herbicides or AHAS Inhibitors

A chemical entity that alters and may fit into the active site of the target protein or bind in any position where it could inhibit activity may be designed by methods known in the art, such as, for example, computer design programs that assist in the design of compounds that specifically interact with a receptor site.

An example of such a program is LUDI (Biosym Technologies—San Diego, Calif.) (see also, Lam, et al., *Science* 263:380, 1994; Thompson, et al., *J. Med. Chem.*, 37:3100, 1994).

The binding pocket and particularly the amino acid residues that have been identified as being involved as inhibitor binding can be used as anchor points for inhibitor design.

The design of site-specific herbicides is advantageous in the control of weed species that may spontaneously develop herbicide resistance in the field, particularly due to mutations in the AHAS gene.

Herbicide-Resistant AHAS Variants: DNA, Vectors, and Polypeptides

The present invention also encompasses isolated DNA molecules encoding variant herbicide-resistant AHAS polypeptides. Genes encoding AHAS polypeptides according to the present invention may be derived from any species and preferably a plant species, and mutations conferring herbicide resistance may be introduced at equivalent positions within any of these AHAS genes. The equivalence of a given codon position in different AHAS genes is a function of both the conservation of primary amino acid sequence and its protein and the retention of similar three-dimensional structure. For example, FIG. 5 illustrates the high degree of sequence homology between AHAS polypeptides derived from different plant species. These AHAS polypeptides exhibit at least about 60 to about 70% overall homology. Without wishing to be bound by theory, it is believed that in regions of the polypeptide having a highly conserved sequence, the polypeptide chain conformation will also be preserved. Thus, it is possible to use an AHAS-encoding sequence from one species for molecular modelling, to introduce mutations predictively into an AHAS gene from a second species for initial testing and iterative improvement, and finally, to introduce the optimized mutations into AHAS derived from yet a third plant species for expression in a transgenic plant.

In one series of embodiment, these AHAS DNAs encode variants of an AHAS polypeptide and preferably of the maize AHAS polypeptide of FIG. 1 (SEQ ID NO:1) in which the polypeptide is modified by substitution at or deletion preceding or following one or more of FIG. 1 (SEQ ID NO:1) amino acid residues P48, G49, S52, M53, E54, A84, A95, T96, S97, G98, P99, G100, A101, V125, R127, R128, M129, I130, G131, T132, D133, F135, Q136, D186, I187, T259, T260, L261, M262, G263, R276, M277, L278, G279, H281, G282, T283, V284, G300, V301, R302, F303, D304, R306, V307, T308, G309, K310, I311, E312, A313, F314, A315, S316, R317, A318, K319, I320, E329, I330, K332, N333, K334, Q335, T404, G413, V414, G415, Q416, H417, Q418, M419, W420, A421, A422, L434, S435, S436, A437, G438, L439, G440, A441, M442, G443, D467, G468, S469, L471, N473, L477, M479, Q495, H496, L497, G498, M499, V501, Q502, Q504, D505, R506, Y508, K509, A510, N511, R512, A513, H514, T515, S524, H572, Q573, E574, H575, V576, L577, P578, M579, I580, P581, G583, G584, functional equivalents of any of the foregoing; insertions or deletions between FIG. 1 (SEQ ID NO:1) Q124 and H150 or functional equivalents thereof; insertions or deletions between FIG. 1 (SEQ ID NO:1) G300 and D324 or functional equivalents thereof; and any combination of any of the foregoing thereof.

The mutations, whether introduced into the polypeptide of FIG. 1 (SEQ ID NO:1) or at equivalent positions in another plant AHAS gene, may comprise alterations in DNA sequence that result in a simple substitution of any one or more other amino acids or deletions of up to 5 amino acid residues proceeding or up to 5 amino acids residues following any of the residence listed above. Suitable amino acid substituents include, but are not limited to, naturally occurring amino acids.

The mutations, whether introduced into the polypeptide of FIG. 1 or at equivalent positions in another plant AHAS gene, may comprise alterations in DNA sequence that result in a simple substitution of any one or more other amino acids or deletions of up to 5 amino acid residues proceeding or up to 5 amino acids residues following any of the residence listed above. Suitable amino acid substituents include, but are not limited to, naturally occurring amino acids.

Alternatively, the mutations may comprise alterations in DNA sequence such that one or more amino acids are added or deleted in frame at the above positions. Preferably, additions comprise about 3 to about 30 nucleotides, and deletions comprise about 3 to about 30 nucleotides. Furthermore, a single mutant polypeptide may contain more than one similar or different mutation.

The present invention encompasses DNA and corresponding RNA sequences, as well as sense and antisense sequences. Nucleic acid sequences encoding AHAS polypeptides may be flanked by natural AHAS regulatory sequences, or may be associated with heterologous sequences, including promoters, enhancers, response elements, signal sequences, polyadenylation sequences, introns, 5'- and 3'-noncoding regions, and the like. Furthermore, the nucleic acids can be modified to alter stability, solubility, binding affinity and specificity. For example, variant AHAS-encoding sequences can be selectively methylated. The nucleic acid sequences of the present invention may also be modified with a label capable of providing a detectable signal, either directly or indirectly. Exemplary labels include radioisotopes, fluorescent molecules, biotin, and the like.

The invention also provides vectors comprising nucleic acids encoding AHAS variants. A large number of vectors, including plasmid and fungal vectors, have been described for expression in a variety of eukaryotic and prokaryotic hosts. Advantageously, vectors may also include a promotor operably linked to the AHAS encoding portion. The encoded AHAS may be expressed by using any suitable vectors and host cells, using methods disclosed or cited herein or otherwise known to those skilled in the relevant art. Examples of suitable vectors include without limitation pBIN-based vectors, pBluescript vectors, and pGEM vectors.

The present invention also encompasses both variant herbicide-resistant AHAS polypeptides or peptide fragments thereof. As explained above, the variant AHAS polypeptides may be derived from the maize polypeptide shown in FIG. 1 or from any plant or microbial AHAS polypeptide, preferably plant AHAS polypeptide. The polypeptides may be further modified by, for example, phosphorylation, sulfation, acylation, glycosylation, or other protein modifications. The polypeptides may be isolated from plants, or from heterologous organisms or cells (including, but not limited to, bacteria, yeast, insect, plant, and mammalian cells) into which the gene encoding a variant AHAS polypeptide has been introduced and expressed. Furthermore, AHAS polypeptides may be modified with a label capable of providing a detectable signal, either directly or indirectly, including radioisotopes, fluorescent compounds, and the like.

Chemical-resistant Plants and Plants Containing Variant AHAS Genes

The present invention encompasses transgenic cells, including, but not limited to seeds, organisms, and plants into which genes encoding herbicide-resistant AHAS variants have been introduced. Non-limiting examples of suitable recipient plants are listed in Table 1 below:

TABLE 1

RECIPIENT PLANTS

| COMMON NAME | FAMILY | LATIN NAME |
| --- | --- | --- |
| Maize | Gramineae | Zea mays |
| Maize, Dent | Gramineae | Zea mays dentiformis |
| Maize, Flint | Gramineae | Zea mays vulgaris |
| Maize, Pop | Gramineae | Zea mays microsperma |
| Maize, Soft | Gramineae | Zea mays amylacea |
| Maize, Sweet | Gramineae | Zea mays amyleasaccharata |
| Maize, Sweet | Gramineae | Zea mays saccharate |
| Maize, Waxy | Gramineae | Zea mays ceratina |
| Wheat, Dinkel | Pooideae | Triticum spelta |
| Wheat, Durum | Pooideae | Triticum durum |
| Wheat, English | Pooideae | Triticum turgidum |
| Wheat, Large Spelt | Pooideae | Triticum spelta |
| Wheat, Polish | Pooideae | Triticum polonium |
| Wheat, Poulard | Pooideae | Triticum turgidum |
| Wheat, Singlegrained | Pooideae | Triticum monococcum |
| Wheat, Small Spelt | Pooideae | Triticum monococcum |
| Wheat, Soft | Pooideae | Triticum aestivum |

TABLE 1-continued

RECIPIENT PLANTS

| COMMON NAME | FAMILY | LATIN NAME |
|---|---|---|
| Rice | Gramineae | *oryza sativa* |
| Rice, American Wild | Gramineae | *Zizania aquatica* |
| Rice, Australian | Gramineae | *Oryza australiensis* |
| Rice, Indian | Gramineae | *Zizania aquatica* |
| Rice, Red | Gramineae | *Oryza glaberrima* |
| Rice, Tuscarora | Gramineae | *Zizania aquatica* |
| Rice, West African | Gramineae | *Oryza glaberrima* |
| Barley | Pooideae | *Hordeum vulgare* |
| Barley, Abyssinian Intermediate, also Irregular | Pooideae | *Hordeum irregulare* |
| Barley, Ancestral Tworow | Pooideae | *Hordeum spontaneum* |
| Barley, Beardless | Pooideae | *Hordeum trifurcatum* |
| Barley, Egyptian | Pooideae | *Hordeum trifurcatum* |
| Barley, fourrowed | Pooideae | *Hordeum vulgare polystichon* |
| Barley, sixrowed | Pooideae | *Hordeum vulgare hexastichon* |
| Barley, Tworowed | Pooideae | *Hordeum distichon* |
| Cotton, Abroma | Dicotyledoneae | *Abroma augusta* |
| Cotton, American Upland | Malvaceae | *Gossypium hirsutum* |
| Cotton, Asiatic Tree, also Indian Tree | Malvaceae | *Gossypium arboreum* |
| Cotton, Brazilian, also, Kidney, and, Pernambuco | Malvaceae | *Gossypium barbadense brasiliense* |
| Cotton, Levant | Malvaceae | *Gossypium herbaceum* |
| Cotton, Long Silk, also Long Sample, Sea Island | Malvaceae | *Gossypium barbadense* |
| Cotton, Mexican, also Short Staple | Malvaceae | *Gossypium hirsutum* |
| Soybean, Soya | Leguminosae | Glycine max |
| Sugar beet | Chenopodiaceae | *Beta vulgaris altissima* |
| Sugar cane | Woody-plant | *Arenga pinnata* |
| Tomato | Solanaceae | *Lycopersicon esculentum* |
| Tomato, Cherry | Solanaceae | *Lycopersicon esculentum cerasiforme* |
| Tomato, Common | Solanaceae | *Lycopersicon esculentum commune* |
| Tomato, Currant | Solanaceae | *Lycopersicon pimpinellifolium* |
| Tomato, Husk | Solanaceae | *Physalis ixocarpa* |
| Tomato, Hyenas | Solanaceae | *Solanum incanum* |
| Tomato, Pear | Solanaceae | *Lycopersicon esculentum pyriforme* |
| Tomato, Tree | Solanaceae | *Cyphomandra betacea* |
| Potato | Solanaceae | *Solanum tuberosum* |
| Potato, Spanish, Sweet potato | Convolvulaceae | *Ipomoea batatas* |
| Rye, Common | Pooideae | *Secale cereale* |
| Rye, Mountain | Pooideae | *Secale montanum* |
| Pepper, Bell | Solanaceae | *Capsicum annuum grossum* |
| Pepper, Bird, also Cayenne, Guinea | Solanaceae | *Capsicum annuum minimum* |
| Pepper, Bonnet | Solanaceae | *Capsicum sinense* |
| Pepper, Bullnose, also Sweet | Solanaceae | *Capsicum annuum grossum* |
| Pepper, Cherry | Solanaceae | *Capsicum annuum cerasiforme* |
| Pepper, Cluster, also Red Cluster | Solanaceae | *Capsicum annuum fasciculatum* |
| Pepper, Cone | Solanaceae | *Capsicum annuum conoides* |
| Pepper, Goat, also Spur | Solanaceae | *Capsicum frutescens* |
| Pepper, Long | Solanaceae | *Capsicum frutescens longum* |
| Pepper, Oranamental Red, also Wrinkled | Solanaceae | *Capsicum annuum abbreviatum* |
| Pepper, Tabasco Red | Solanaceae | *Capsicum annuum conoides* |
| Lettuce, Garden | Compositae | *Lactuca saliva* |
| Lettuce, Asparagus, also Celery | Compositae | *Lactuca saliva asparagina* |
| Lettuce, Blue | Compositae | *Lactuca perennis* |
| Lettuce, Blue, also Chicory | Compositae | *Lactuca pulchella* |
| Lettuce, Cabbage, also Head | Compositae | *Lactuca saliva capitata* |
| Lettuce, Cos, also Longleaf, Romaine | Compositae | *Lactuca sativa longifolia* |
| Lettuce, Crinkle, also Curled, Cutting, Leaf | Compositae | *Lactuca sativa crispa* |
| Celery | Umbelliferae | *Apium graveolens dulce* |
| Celery, Blanching, also Garden | Umbelliferae | *Apium graveolens dulce* |
| Celery, Root, also Turniprooted | Umbelliferae | *Apium graveolens rapaceum* |
| Eggplant, Garden | Solanaceae | *Solanum melongena* |
| Sorghum | Sorghum | All crop species |
| Alfalfa | Leguminosae | *Medicago sativum* |
| Carrot | Umbelliferae | *Daucus carota sativa* |
| Bean, Climbing | Leguminosae | *Phaseolus vulgaris vulgaris* |
| Bean, Sprouts | Leguminosae | *Phaseolus aureus* |
| Bean, Brazilian Broad | Leguminosae | *Canavalia ensiformis* |
| Bean, Broad | Leguminosae | *Vicia faba* |
| Bean, Common, also French, White, Kidney | Leguminosae | *Phaseolus vulgaris* |
| Bean, Egyptian | Leguminosae | *Dolichos lablab* |
| Bean, Long, also Yardlong | Leguminosae | *Vigna sesquipedalis* |
| Bean, Winged | Leguminosae | *Psophocarpus tetragonolobus* |
| Oat, also Common, Side, Tree | Avena | *Sativa* |
| Oat, Black, also Bristle, Lopsided | Avena | *Strigosa* |
| Oat, Bristle | Avena | |
| Pea, also Garden, Green, Shelling | Leguminosae | *Pisum, sativum sativum* |
| Pea, Blackeyed | Leguminosae | *Vigna sinensis* |
| Pea, Edible Podded | Leguminosae | *Pisum sativum axiphium* |
| Pea, Grey | Leguminosae | *Pisum sativum speciosum* |
| Pea, Winged | Leguminosae | *Tetragonolobus purpureus* |

TABLE 1-continued

RECIPIENT PLANTS

| COMMON NAME | FAMILY | LATIN NAME |
|---|---|---|
| Pea, Wrinkled | Leguminosae | Pisum sativum medullare |
| Sunflower | Compositae | Helianthus annuus |
| Squash, Autumn, Winter | Dicotyledoneae | Cucurbita maxima |
| Squash, Bush, also Summer | Dicotyledoneae | Cucurbita pepo melopepo |
| Squash, Turban | Dicotyledoneae | Cucurbita maxima turbaniformis |
| Cucumber | Dicotyledoneae | Cucumis sativus |
| Cucumber, African, also Bitter | | Momordica charantia |
| Cucumber, Squirting, also Wild | | Ecballium elaterium |
| Cucumber, Wild | | Cucumis anguria |
| Poplar, California | Woody-Plant | Populus trichocarpa |
| Poplar, European Black | | Populus nigra |
| Poplar, Gray | | Populus canescens |
| Poplar, Lombardy | | Populus italica |
| Poplar, Silverleaf, also White | | Populus alba |
| Poplar, Western Balsam | | Populus trichocarpa |
| Tobacco | Solanaceae | Nicotiana |
| Arabidopsis Thaliana | Cruciferae | Arabidopsis thaliana |
| Turfgrass | Lolium | |
| Turfgrass | Agrostis Other families of turfgrass | |
| Clover | Leguminosae | |

Expression of the variant AHAS polypeptides in transgenic plants confers a high level of resistance to herbicides including, but not limited to, imidazolinone herbicides such as, for example, imazethapyr (PURSUIT®), allowing the use of these herbicides during cultivation of the transgenic plants.

Methods for the introduction of foreign genes into plants are known in the art. Non-limiting examples of such methods include Agrobacterium infection, particle bombardment, polyethylene glycol (PEG) treatment of protoplasts, electroporation of protoplasts, microinjection, macroinjection, tiller injection, pollen tube pathway, dry seed imbibition, laser perforation, and electrophoresis. These methods are described in, for example, B. Jenes et al., and S. W. Ritchie et al. In *Transgenic Plants, Vol. 1, Engineering and Utilization*, ed. S.-D. Kung, R. Wu, Academic Press, Inc., Harcourt Brace Jovanovich 1993; and L. Mannonen et al., *Critical Reviews in Biotechnology*, 14:287–310, 1994.

In a preferred embodiment, the DNA encoding a variant AHAS is cloned into a DNA vector containing an antibiotic resistance marker gene, and the recombinant AHAS DNA-containing plasmid is introduced into *Agrobacterium tumefaciens* containing a Ti plasmid. This "binary vector system" is described in, for example, U.S. Pat. No. 4,490,838, and in An et al., *Plant Mol.Biol.Manual* A3:1–19 (1988). The transformed Agrobacterium is then co-cultivated with leaf disks from the recipient plant to allow infection and transformation of plant cells. Transformed plant cells are then cultivated in regeneration medium, which promotes the formation of shoots, first in the presence of the appropriate antibiotic to select for transformed cells, then in the presence of herbicide. In plant cells successfully transformed with DNA encoding herbicide-resistant AHAS, shoot formation occurs even in the presence of levels of herbicide that inhibit shoot formation from non-transformed cells. After confirming the presence of variant AHAS DNA using, for example, polymerase chain reaction (PCR) analysis, transformed plants are tested for their ability to withstand herbicide spraying and for their capabilities for seed germination and root initiation and proliferation in the presence of herbicide.

Other Applications

The methods and compositions of the present invention can be used in the structure-based rational design of herbicide-resistant AHAS variants, which can be incorporated into plants to confer selective herbicide resistance on the plants. Intermediate variants of AHAS (for example, variants that exhibit sub-optimal specific activity but high resistance and selectivity, or the converse) are useful as templates for the design of second-generation AHAS variants that retain adequate specific activity and high resistance and selectivity.

Herbicide resistant AHAS genes can be transformed into crop species in single or multiple copies to confer herbicide resistance. Genetic engineering of crop species with reduced sensitivity to herbicides can:

(1) Increase the spectrum and flexibility of application of specific effective and environmentally benign herbicides such as imidazolinone herbicides;

(2) Enhance the commercial value of these herbicides;

(3) Reduce weed pressure in crop fields by effective use of herbicides on herbicide resistant crop species and a corresponding increase in harvest yields;

(4) Increase sales of seed for herbicide-resistant plants;

(5) Increase resistance to crop damage from carry-over of herbicides applied in a previous planting;

(6) Decrease susceptibility to changes in herbicide characteristics due to adverse climate conditions; and (7) Increase tolerance to unevenly or mis-applied herbicides.

For example, transgenic AHAS variant protein containing plants can be cultivated. The crop can be treated with a weed controlling effective amount of the herbicide to which the AHAS variant transgenic plant is resistant, resulting in weed control in the crop without detrimentally affecting the cultivated crop.

The DNA vectors described above that encode herbicide-resistant AHAS variants can be further utilized so that expression of the AHAS variant provides a selectable marker for transformation of cells by the vector. The intended recipient cells may be in culture or in situ, and the AHAS variant genes may be used alone or in combination with other selectable markers. The only requirement is that the recipient cell is sensitive to the cytotoxic effects of the cognate herbicide. This embodiment takes advantage of the relative low cost and lack of toxicity of, for example, imidazolinone-based herbicides, and may be applied in any system that requires DNA-mediated transformation.

Exemplification with respect to Preferred Embodiments

The following examples are intended to illustrate the present invention without limitation.

EXAMPLE 1

Design of Herbicide-resistant AHAS Variants

Residues located close to the proposed herbicide binding site of the model described in detail above were selected for mutagenesis in order to design an active AHAS polypeptide with decreased herbicide binding capacity. Each site at the surface of the pocket was considered in terms of potential interactions with other residues in the pocket, as well as with cofactors and herbicides. For example, addition of positively charged residue(s) is expected to interfere with the charge distribution within the binding site, resulting in a loss in affinity of binding of a negatively-charged herbicide.

Three residues were identified as most useful targets for mutagenesis:

(1) F135 was believed to interact with both the isoalloxazine ring of FAD and with the aromatic group of the herbicides. In accordance with the strategy of introducing more charged residues into the binding pocket, this residue was changed to arginine.

(2) M53 contacts helix 498–507. This helix contains known herbicide resistance mutation sites and is also implicated in TPP binding. Furthermore, substitution of glutamic acid at position 53 was believed to favor an interaction with K185, reducing the affinity of K185 for the carboxylate group of imazethapyr.

(3) R128 is located near the entrance to the pocket, where it was believed to be involved in the initial transport of charged herbicides into the binding pocket. This residue was changed to alanine to remove both its charge and its long hydrophobic side chain.

EXAMPLE 2

Site-directed Mutagenesis of AHAS to Produce Herbicide-resistant Variants

Figure 6:
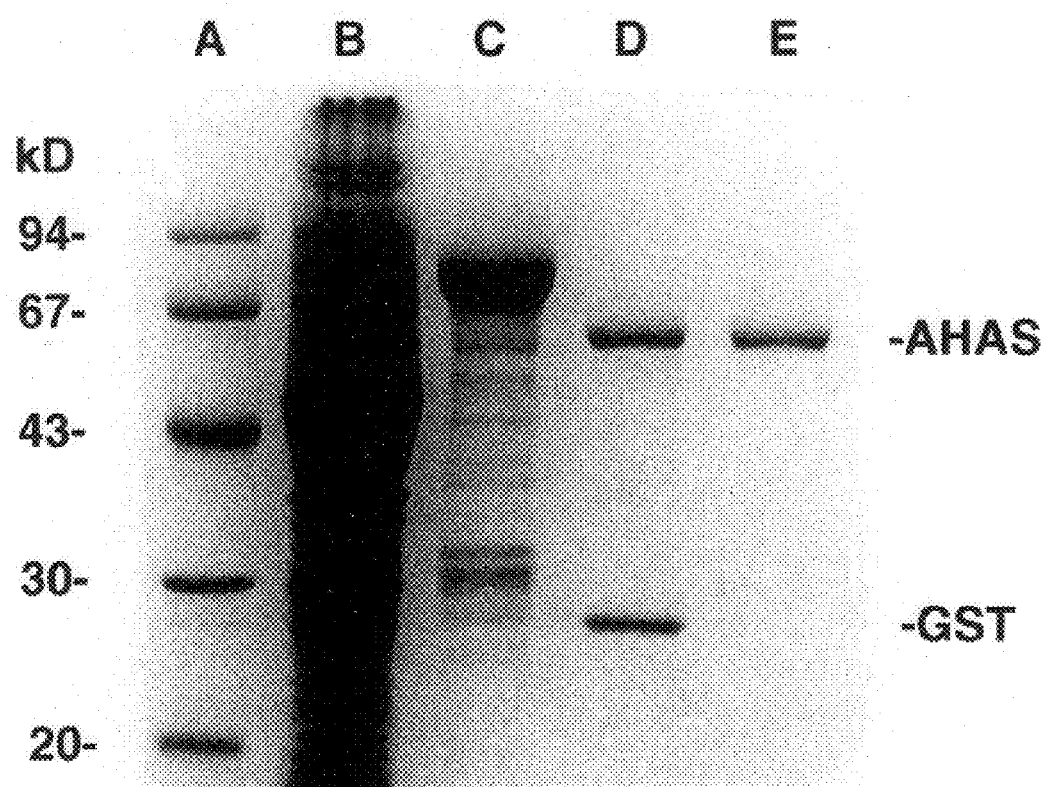
FIG. 6 is a photographic illustration of an SDS-polyacrylamide gel stained for protein showing purification of maize AHAS. The lanes contain (from left to right): A, Molecular weight markers; B, Crude *E. coli* cell extract; C, Glutathione-agarose affinity purified preparation; D, Thrombin digest of the affinity purified preparation; E, Second pass through glutathione-agarose column and Sephacryl S-100 gel filtration.

The Arabidopsis AHAS gene was inserted in-frame to the 3' end of the coding region of the glutathione S-transferase gene in the pGEX-2T vector (Pharmacia). Construction of the vector in this manner maintained the six amino acid thrombin recognition sequence at the junction of the expressed glutathione-S-transferase (GST)/AHAS fusion protein. Thrombin digestion of the expressed fusion protein results in an AHAS protein with an N-terminal starting position at the end of the transit peptide at a putative transit peptide processing site, with a residual N-terminal glycine derived from the thrombin recognition site. The final amino terminus of the cleaved AHAS protein consists of Gly-Ser-Ser-Ile-Ser. Site-directed mutations were introduced into the AHAS gene in this vector.

Site-directed mutations were constructed according to the PCR method of Higuchi (*Recombinant PCR.* In MA Innis, et al. *PCR Protocols: A Guide to Methods and Applications,* Academic Press, San Diego, pp. 177–183, 1990). Two PCR products, each of which overlap the mutation site, were amplified. The primers in the overlap region contained the mutation. The overlapping PCR amplified fragments were combined, denatured, and allowed to re-anneal together, producing two possible heteroduplex products with recessed 3'-ends. The recessed 3'-ends were extended by Taq DNA polymerase to produce a fragment that was the sum of the two overlapping PCR products containing the desired mutation. A subsequent re-amplification of this fragment with only the two "outside" primers resulted in the enrichment of the full-length product. The product containing the mutation was then re-introduced into the Arabidopsis AHAS gene in the pGEX-2T vector.

EXAMPLE 3

Expression and Purification of AHAS Variants

A. Methods

*E. coli* (DH5α) cells transformed with the pGEX-2T vector containing either the maize wild type AHAS gene (vector designation pAC751), the Arabidopsis Ser653Asn mutant, or the Arabidopsis Ile401Phe mutant were grown overnight in LB broth containing 50 μg/mL ampicillin. The overnight culture of *E. coli* was diluted 1:10 in 1 L LB, 50 μg/mL ampicillin, and 0.1% v/v antifoam A. The culture was incubated at 37° C. with shaking until the $OD_{600}$ reached approximately 0.8. Isopropylthiogalactose (IPTG) was added to a final concentration of 1 mM and the culture was incubated for 3 more hours.

Cells were harvested by centrifugation at 8,670×g for 10 minutes in a JA-10 rotor and resuspended in 1/100th of the original culture volume in MTPBS (16 mM $Na_2HPO_4$, 4 mM $NaH_2PO_4$, 150 mM NaCl, pH 7.3). Triton X-100 and lysozyme were added to a final concentration of 1% v/v and 100 μg/mL, respectively. Cells were incubated at 30° C. for 15 minutes cooled to 4° C. on ice, and were lysed by sonication for 10 seconds at level 7 with a Branson Sonifier Cell Disrupter equipped with a microtip probe. The cell free extract was centrifuged at 35,000×g for 10 min. at 4° C. The supernatant was decanted and the centrifugation step was repeated.

Purification of expressed fusion proteins was performed as modified from Smith and Johnson (Gene 67:31–40, 1988). The supernatant was warmed to room temperature and was passed through a 2 mL column of glutathione-agarose beads (sulfur linkage, Sigma) equilibrated in MTPBS. The column was subsequently washed with MTPBS at room temperature until the $A_{280}$ of eluant matched that of MTPBS. The fusion protein was then eluted using a solution containing 5 mM reduced glutathione in 50 mM Tris HCL, pH 8.0. The eluted fusion protein was treated with approximately 30 NIH units of thrombin and dialyzed against 50 mM citrate pH 6.5 and 150 mM NaCl.

The fusion protein was digested overnight at room temperature. Digested samples were dialyzed against MTPBS and passed twice through a glutathione-agarose column equilibrated in MTPBS to remove the released glutathione transferase protein. The protein fraction that did not bind to the column was collected and was concentrated by ultrafiltration on a YM10 filter (Amicon). The concentrated sample was loaded onto a 1.5×95 cm Sephacryl S-100 gel filtration column equilibrated in gel filtration buffer (50 mM HEPES, 150 mM NaCl, pH 7.0). Two mL fractions were collected at a flow rate of 0.14 mL/min. Enzyme stability was tested by storage of the enzyme at 4° C. in gel filtration buffer with the addition of 0.02% sodium azide and in the presence or absence of 2 mM thiamine pyrophosphate and 100 μM flavin adenine dinucleotide (FAD).

B. Results

*E. coli* transformed with the pAC751 plasmid containing the wide-type AHAS gene fused downstream and in-frame with the GST gene expressed a 91 kD protein when induced with IPTG. The 91 kD protein exhibited the predicted molecular mass of a GST/AHAS fusion protein (the sum of 26 kD and 65 kD, respectively). When the cell free extract of DH5α/pAC751 was passed through a glutathione-agarose affinity gel, washed, and eluted with free glutathione it yielded a preparation enriched in the 91 kD protein (FIG. 6, lane C). The six amino acid thrombin recognition site engineered in the junction of GST and AHAS was successfully cleaved by thrombin (FIG. 6, lane D). The cleaved fusion protein preparation consisted of the expected 26 kD GST protein and the 65 kD maize AHAS protein. Maize AHAS was purified to homogeneity by a second pass through the glutathione-agarose column to affinity subtract GST and subjected to a final Sephacryl S-100 gel filtration step to eliminated thrombin (FIG. 6, lane E). The 65 kD protein is recognized on western blots by a monoclonal antibody raised against a maize AHAS peptide.

Purified wild type maize AHAS was analyzed by electrospray mass spectrometry and was determined to have a molecular mass of 64,996 daltons (data not shown). The predicted mass, as calculated from the deduced amino acid sequence of the gene inserted into the pGEX-2T vector, is 65,058. The 0.096% discrepancy between the empirically determined and predicted mass was within tuning variability of the mass spectrometer. The close proximity of the two mass determinations suggests that there were no misincorporated nucleotides during construction of the expression vector, nor any post-translational modifications to the protein that would cause gross changes in molecular mass. Moreover, the lack of spurious peaks in the preparation of purified enzyme indicated that the sample was free of contamination.

EXAMPLE 4

Enzymatic Properties of AHAS Variants

The enzymatic properties of wild-type and variant AHAS produced in E. coli were measured by a modification of the method of Singh et al. (Anal. Biochem 211:173–179, 1988) as follows:

A reaction mixture containing 1× AHAS assay buffer (50 mM HEPES pH 7.0, 100 mM pyruvate, 10 mM $MgCl_2$, 1 mM thiamine pyrophosphate (TPP), and 50 µM flavin adenine dinucleotide (FAD)) was obtained either by dilution of enzyme in 2× assay buffer or by addition of concentrated enzyme to 1× AHAS assay buffer. All assays containing imazethapyr and associated controls contained a final concentration of 5% DMSO due to addition of imazethapyr to assay mixtures as a 50% DMSO solution. Assays were performed in a final volume of 250 µL at 37° C. in microtiter plates. After allowing the reaction to proceed for 60 minutes, acetolactate accumulation was measured calorimetrically as described by Singh et al., Anal. Biochem 171:173–179, 1988.

Maize AHAS expressed and purified from pAC751 as described in Example 3 above is active in the conversion of pyruvate to acetolactate. Full AHAS activity is dependent on the presence of the cofactors FAD and TPP in the assay medium. No activity was detected when only FAD was added to the assay medium. The activity of the purified enzyme with TPP only, or with no cofactors, was less than 1% of the activity detected in the presence of both TPP and FAD. Normally, AHAS present in crude plant extracts is very labile, particularly in the absence of substrate and cofactors. In contrast, the purified AHAS from the bacterial expression system showed no lose in catalytic activity when stored for one month at 4° C. in 50 mm HEPES pH 7.0, 150 mM NaCl, 0.02% $NaN_3$ in the presence or absence of FAD and TPP. Furthermore, no degradation products were visible from these stored preparations when resolved in SDS-PAGE gels.

The specific activities of wild-type AHAS and the M124E, R199A, and F206R variants are shown in Table 2 below. As determined from the alignment in FIG. 5, the M124E mutation in Arabidopsis AHAS is the equivalent of the maize M53E mutation, the R199A mutation in Arabidopsis is the equivalent of the maize R128A mutation, and the F206R mutation in Arabidopsis is the equivalent of the maize F135R mutation. The mutations designed in the maize AHAS structural model were used to identify the equivalent amino acid in the dicot Arabidopsis AHAS gene and were incorporated and tested in the Arabidopsis AHAS gene. This translation and incorporation of rationally designed herbicide mutations into the dicot Arabidopsis AHAS gene can facilitate evaluation of herbicide resistance in plants of a dicot species.

TABLE 2

| SPECIFIC ACTIVITY | | |
| --- | --- | --- |
|  | Specific Activity | % Catalytic Activity as Compared to Wild Type |
| Wild-Type | 99.8 | 100 |
| Met124Glu | 9.15 | 9.16 |
| Arg199Ala | 86.3 | 86.5 |
| Phe206Arg | 5.07 | 5.1 |

Figure 7:
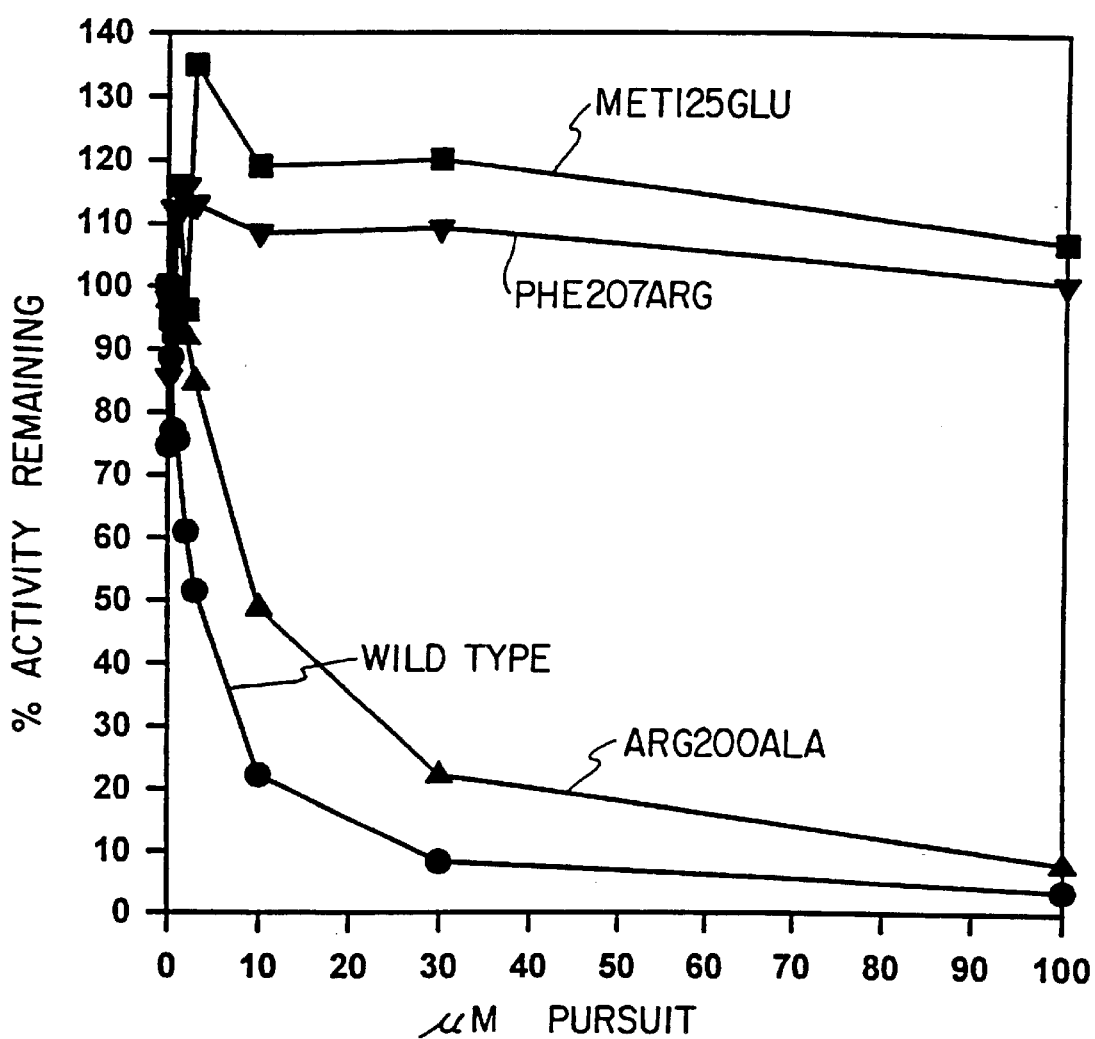
FIG. 7 is a graphic illustration of the results of in vitro assays of the enzymatic activity of wild-type and mutant AHAS proteins in the absence and in the presence of increasing concentrations of imazethapyr (PURSUIT® herbicide). The Y axis represents the % of activity of the mutant enzyme, wherein the 100% value is measured in the absence of inhibitor.
Figure 8:
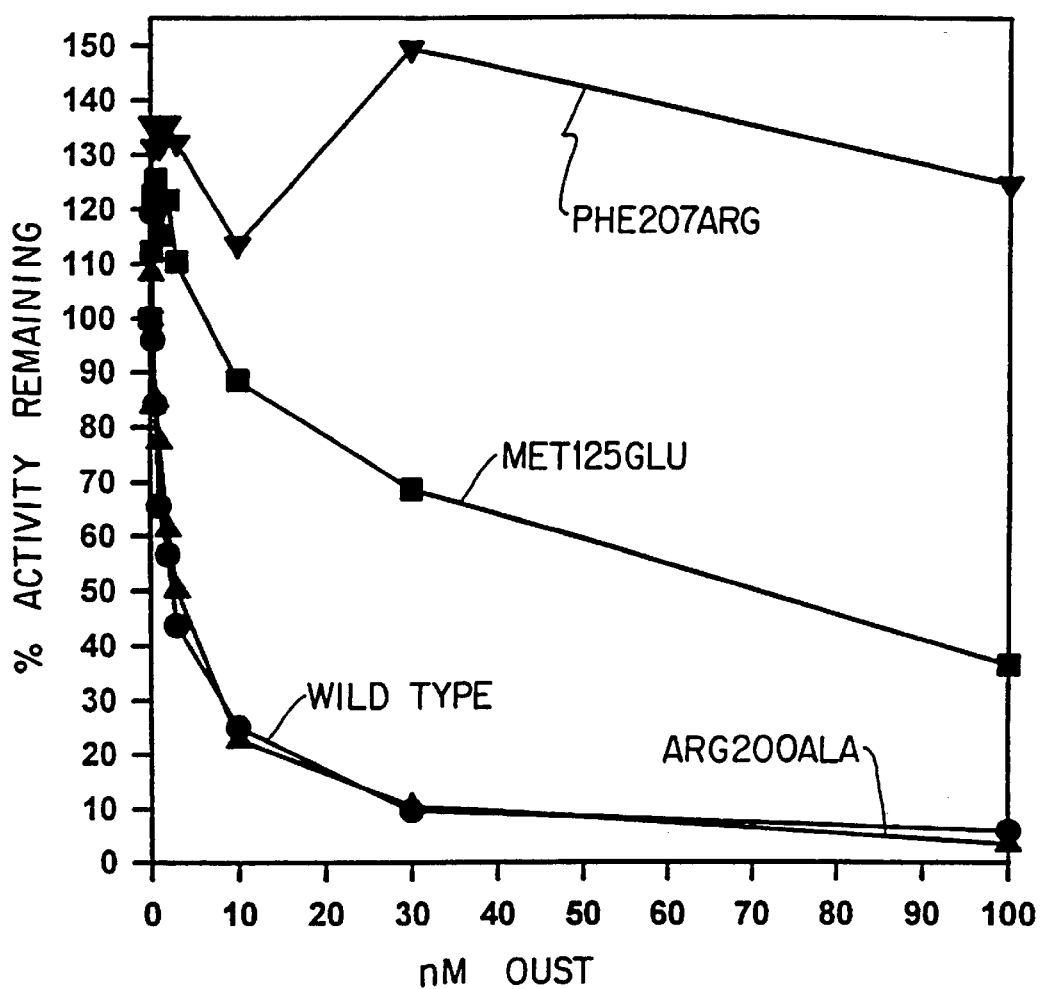
FIG. 8 is a graphic illustration of the results of in vitro assays of the enzymatic activity of wild-type and mutant AHAS proteins in the absence and presence of increasing concentrations of sulfometuron methyl (OUST® herbicide). The Y axis represents the % of activity of the mutant enzyme, wherein the 100% value is measured in the absence of inhibitor.

The R199A mutation maintains a high level of catalytic activity (Table 2) while exhibiting a significant level of resistance to imazethapyr (FIG. 7). Notably, this variant retains complete sensitivity to sulfonylureas (FIG. 8). Thus, this variant fulfills the criteria of high specific activity and selective herbicide resistance. By contrast, the M124E substitution resulted in almost complete resistance to imazethapyr (FIG. 7) but also exhibited severely reduced catalytic activity (Table 2). Relative to imidazolinone resistance, this variant exhibits greater sensitivity to sulfonylurea (FIG. 8), suggesting that this residue is a good candidate for creating a mutation that confers selective resistance. Substitution of an amino acid other than glutamic acid may help to maintain catalytic activity. The F206R substitution yielded similar results to those observed with M124E variant, but lacked selectivity in resistance.

EXAMPLE 5

Iterative Improvement of AHAS Herbicide-Resistant Variant Using a Rational Design Approach Changing residue 124 in AHAS from Met to Glu as described in Example 4 above conferred imidazolinone resistance but also reduced enzymatic activity to 9.2% of the wild type value. The model of the maize AHAS structure described above suggested that Met53 (equivalent to the Arabidopsis Met124 residue) interacts with a series of hydrophobic residues on the face of an α-helix that is derived from a separate subunit but are in close proximity to Met53. Thus, the hydrophobic interaction between Met53 and the residues on the helix may stabilize both subunit/subunit association and the conformation of the active site. It was believed that the substitution of the hydrophobic Met residue with a charged glutamate residue most probably destabilizes the inter-subunit hydrophobic interaction and results in a loss of catalytic activity.

Figure 9:
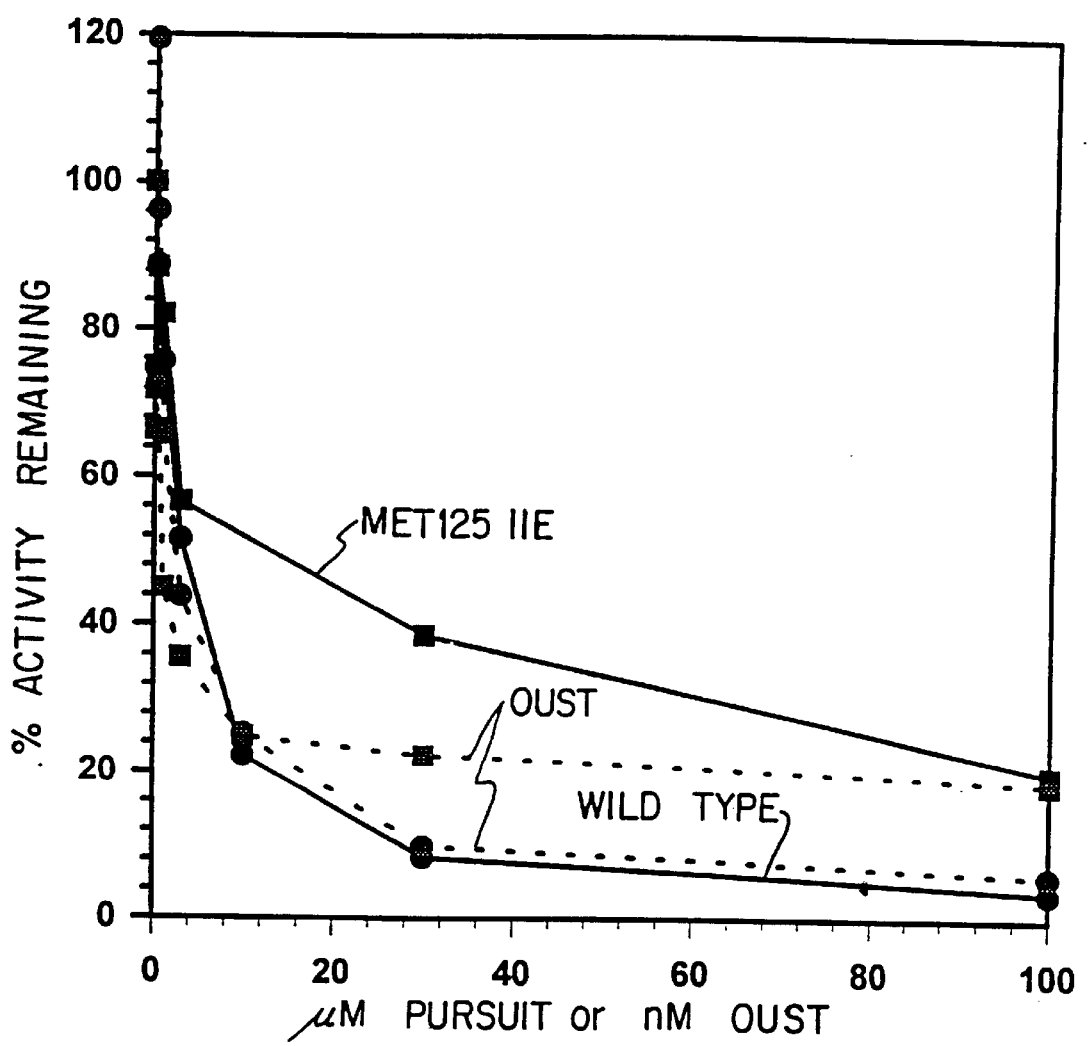
FIG. 9 is a graphic illustration of in vitro assays of the enzymatic activity of wild-type Arabidopsis AHAS protein and the Met124Ile mutant Arabidopsis AHAS protein in the absence and presence of increasing concentrations of imazethapyr (PURSUIT® herbicide) and sulfometuron methyl (OUST® herbicide). The Y axis represents the % activity of the mutant enzyme, wherein the 100% value is measured in the absence of inhibitor.

Based on this structure/function analysis, the activity of the original Arabidopsis Met124Glu (equivalent to maize Met53Glu) mutant enzyme was then iteratively improved by substituting a more hydrophobic amino acid (Ile) at this position. The hydrophobic nature of the Ile side chain resulted in restoration of activity to wild type levels (specific activity of 102, equivalent to 102% of the wild-type activity), but the greater bulk of the Ile side chain was still able to maintain a significant level of imidazolinone resistance (FIG. 9).

Figure 10:
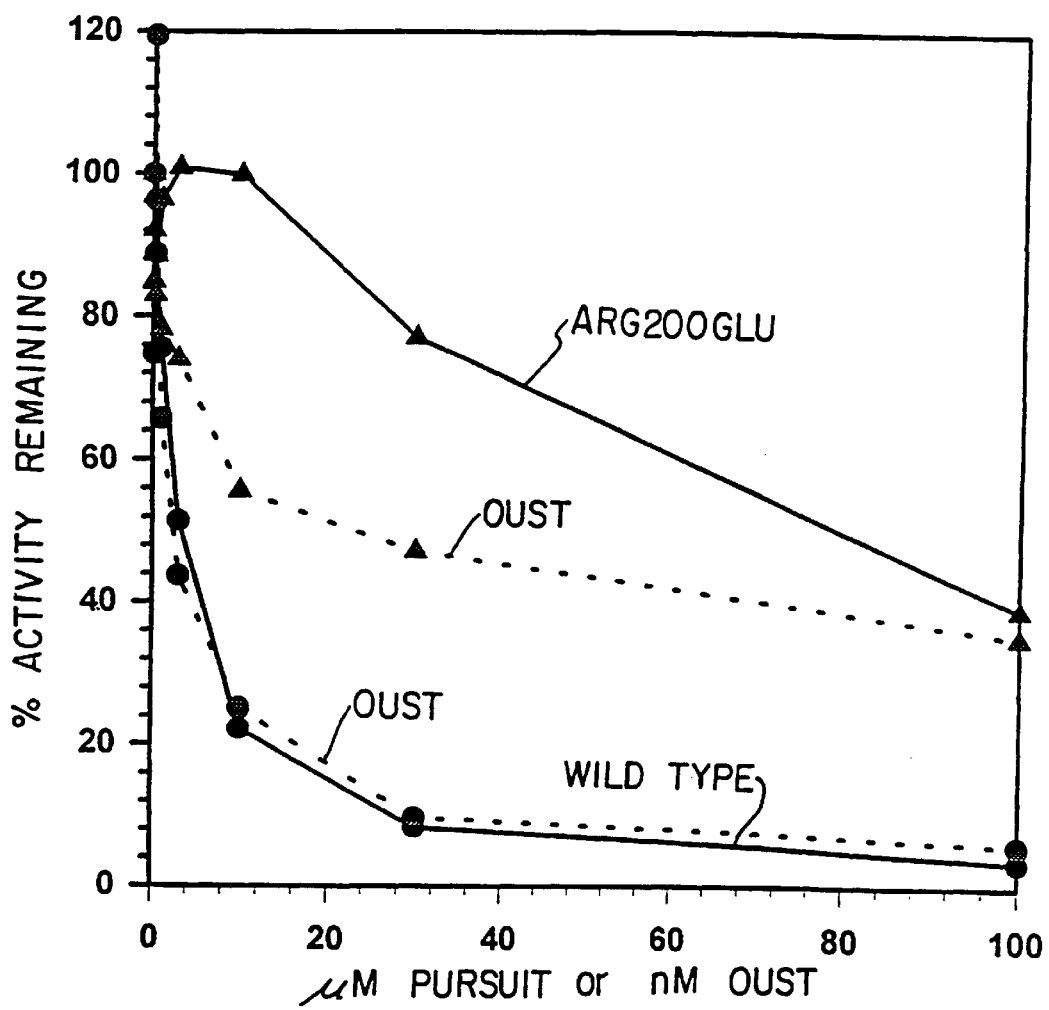
FIG. 10 is a graphic illustration of in vitro assays of the enzymatic activity of wild-type Arabidopsis AHAS protein and the Met124His mutant Arabidopsis AHAS protein in the absence and presence of increasing concentrations of imazethapyr (PURSUIT® herbicide) and sulfometuron methyl (OUST® herbicide). The Y axis represents the % activity of the mutant enzyme, wherein the 100% value is measured in the absence of inhibitor.

By comparison, substitution of a histidine residue at this position resulting in an AHAS variant exhibiting a specific activity of 42.5, equivalent to 42.6% of the wild-type activity. This mutant, nonetheless, exhibited a high degree of resistance to PURSUIT® (FIG. 10).

EXAMPLE 6

Figure 11:
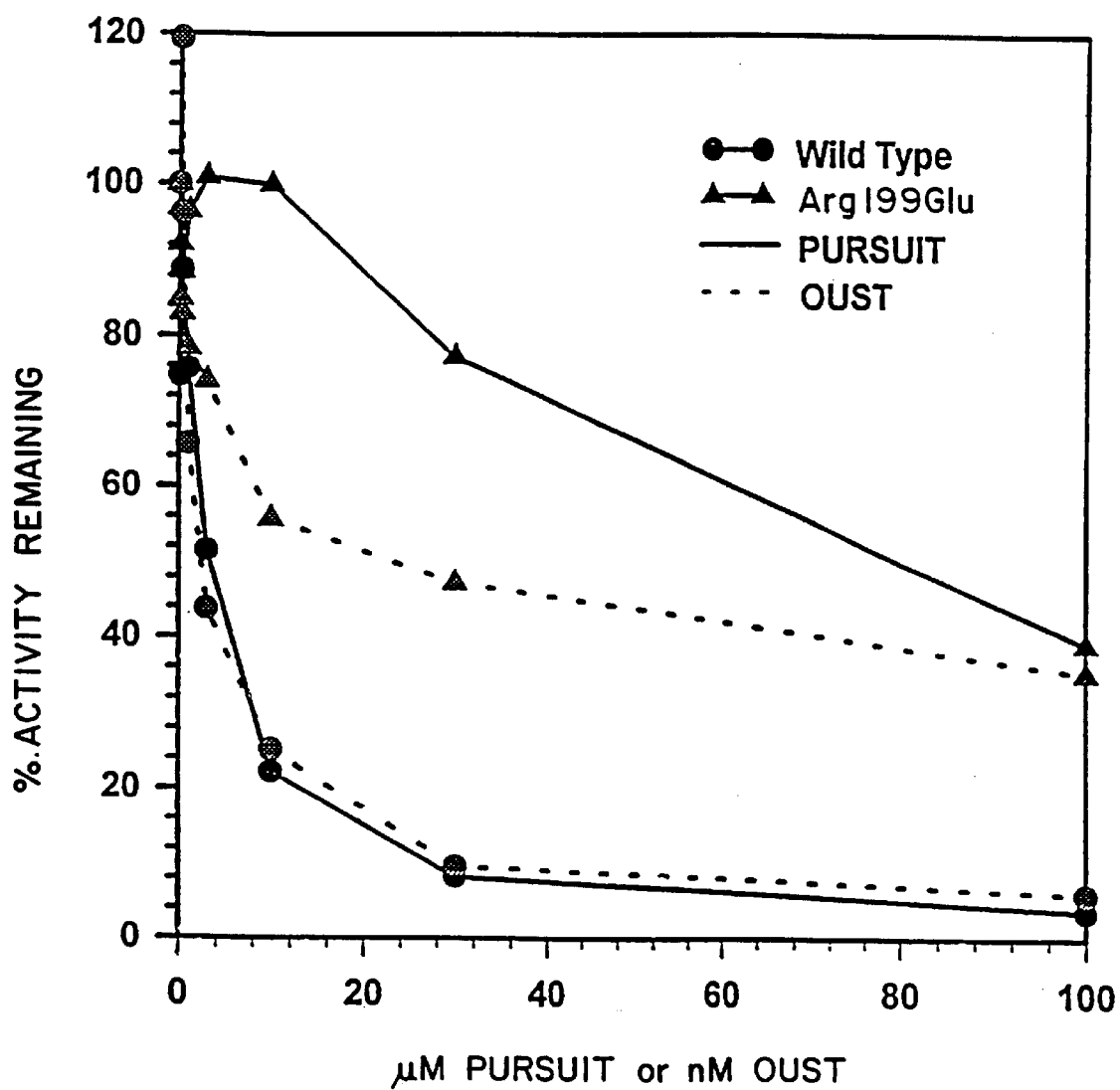
FIG. 11 is a graphic illustration of in vitro assays of the enzymatic activity of wild-type Arabidopsis AHAS protein and Arg199Glu mutant Arabidopsis AHAS protein in the absence and presence of increasing concentrations of imazethapyr (PURSUIT® herbicide) and sulfometuron methyl (OUST® herbicide). The Y axis represents the % activity of the mutant enzyme, wherein the 100% value is measured in the absence of inhibitor.

Iterative Improvement of AHAS Herbicide-Resistant Variant Using a Rational Design Approach Another example of iterative refinement using the methods of the present invention involves the Arg128Ala variant. The structural model of maize AHAS suggested that the Arg128 residue, which resides at the lip of the herbicide binding pocket, contributes to channeling charged substrates and herbicides into the herbicide binding pocket and into the active site. The Arg 128 residue is distant from the TPP moiety, which binds the initial pyruvate molecule in the reaction mechanism of AHAS, explaining why the substitution of Arabidopsis AHAS Arg199 (the equivalent to maize Arg128) to alanine had little effect on the catalytic activity of the enzyme. The structural model further indicated that a more radical change could be made at this position to raise the level of resistance while maintaining high levels of catalytic activity. On this basis, an iterative improvement of the mutation was made to substitute the positively charge arginine residue with a negatively charged glutamate residue. The enzyme thus mutated had improved levels of resistance to PURSUIT® while maintaining high levels of activity (specific activity of 114, equivalent to 114% of the wild-type activity) (FIG. 11).

EXAMPLE 7

Interchangeability of AHAS Derived from Different Species in Structure-Based Rational Design of Herbicide-Resistant AHAS Variants A structural model of the three-dimensional structure of AHAS is built with a monocot AHAS sequence such as that derived from maize, as described above. To introduce mutations into AHAS derived from a dicot species such as Arabidopsis, the sequences of AHAS derived from the monocot and dicot species are aligned using the GAP and PILEUP programs (Genetics Computer Group, 575 Sequence Drive, Madison, Wis. 53711). Equivalent positions are determined from the computer-generated alignment. The mutations are then introduced into the dicot AHAS gene as described above. Following expression of the mutant AHAS protein in *E. coli* and assessment of its biochemical properties (i.e., specific activity and resistance to herbicides), the mutant gene is introduced into a dicot plant by plant transformation methods as described above.

EXAMPLE 8

Figure 12:
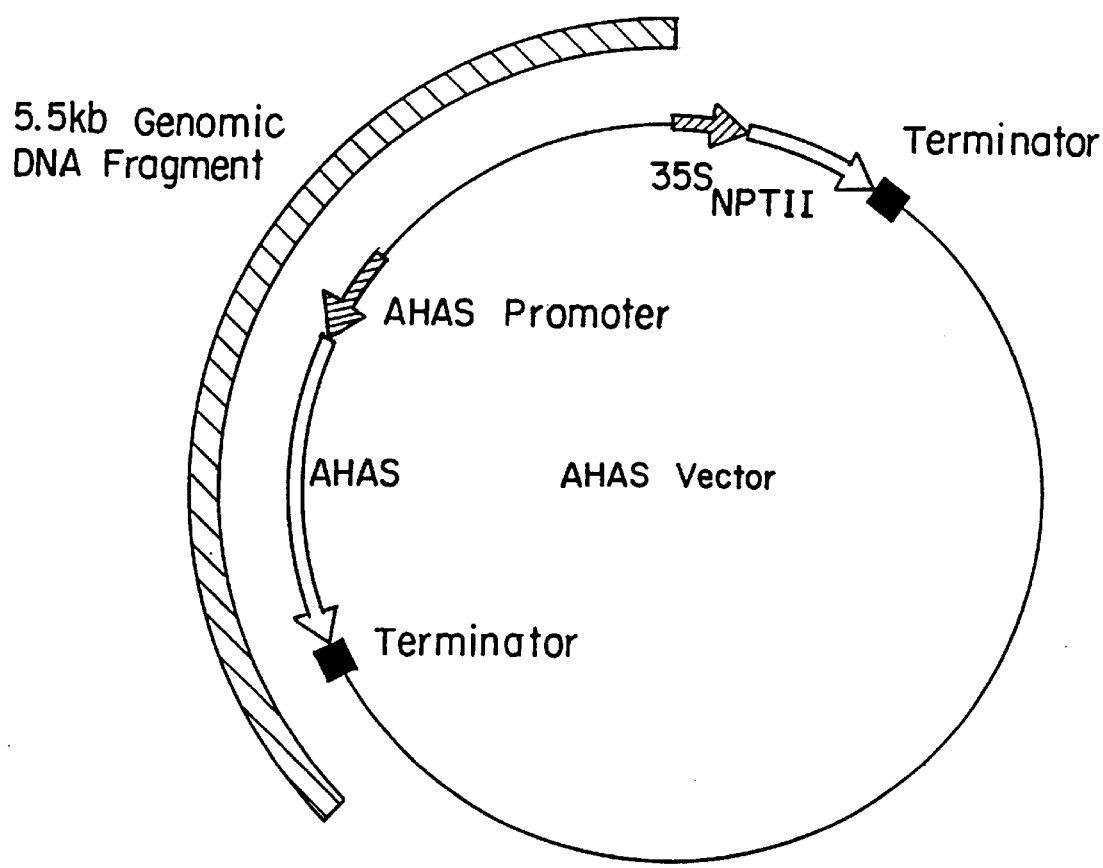
FIG. 12 is a schematic illustration of a DNA vector used for plant transformation, which contains the nptII gene (encoding kanamycin resistance) under the control of the 35S promoter and an AHAS gene (wild type or variant) under the control of the Arabidopsis AHAS promoter.

Production of Herbicide-Resistant Plants by Transformation with Rationally Designed AHAS Genes DNA Constructs:

Rationally designed AHAS variant genes contained within *E. coli* expression vectors were used as a source of DNA restriction fragments to replace the equivalent restriction fragment in a Arabidopsis AHAS gene. This gene is present in a 5.5 kb genomic DNA fragment which also contains the Arabidopsis AHAS promoter, the Arabidopsis AHAS termination sequence and 5'- and 3'-flanking DNA. After DNA sequencing through the mutation sites was performed to confirm the presence of the proper mutation, the entire 5.5 kb fragment from each plasmid was inserted into a pBIN based plant transformation vector (Mogen, Leiden, Netherlands). The plant transformation vector also contains the neomycin phosphotransferase II (nptII) kanamycin resistance gene driven by the 35S cauliflower mosaic virus promoter. The final vector construct is displayed in FIG. 12. Vectors containing Arabidopsis AHAS genes with Met124Ile, Met124His, and Arg199Glu mutations (corresponding to Met53Ile, Met53His, and Arg128Glu mutations in the maize AHAS sequence as shown in FIG. 1) were labeled pJK002, pJK003, and pJK004, respectively.

Each of these vectors was transformed into *Agrobacterium tumefaciens* strain LBA4404 (R&D Life Technologies, Gaithersburg, Md.) using the transformation method described in An et al., *Plant Mol.Biol.Manual* A3:1–19 (1988).

Plant Transformation:

Leaf disc transformation of *Nicotiana tabacum* cv. Wisconsin 38 was performed as described by Horsch et al. (*Science,* 227: 1229–1231, 1985) with slight modifications. Leaf discs were cut from plants grown under sterile conditions and co-cultivated upsidedown in Murashige Skoog media (Sigma Chemical Co., St. Louis, Mo.) for 2–3 days at 25° C. in darkness with *Agrobacterium tumefaciens* strains containing plasmids pJK002, pJK003, or pJK004. The discs were blotted dry and transferred to regeneration Murashige Skoog medium with B5 vitamins containing 1 mg/L benzyladenine and 0.1 mg/l 1-Napthyl Acetic Acid, 100 mg/L kanamycin, and 500 mg/L cefotaxime (all obtained from Sigma).

Initially, transformants were selected by kanamycin resistance conferred by the nptII gene present in the transformation vector. Shoots derived from the leaf discs were excised and placed on fresh Murashige Skoog hormone free media containing cefotaxime and kanamycin.

In Vivo Herbicide Resistance

Figure 13:
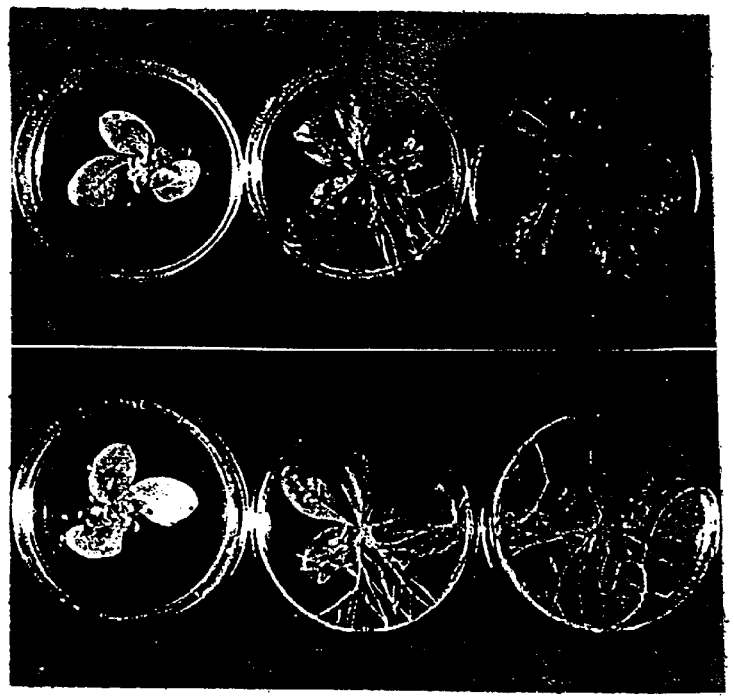
FIG. 13 is a photograph showing the root development of tobacco plants transformed with the Arabidopsis AHAS gene containing either the Met124Ile or Arg199Glu mutation and a non-transformed control. Plants were grown for 18 days after transfer into medium containing 0.25 µM imazethapyr.
Figure 14:
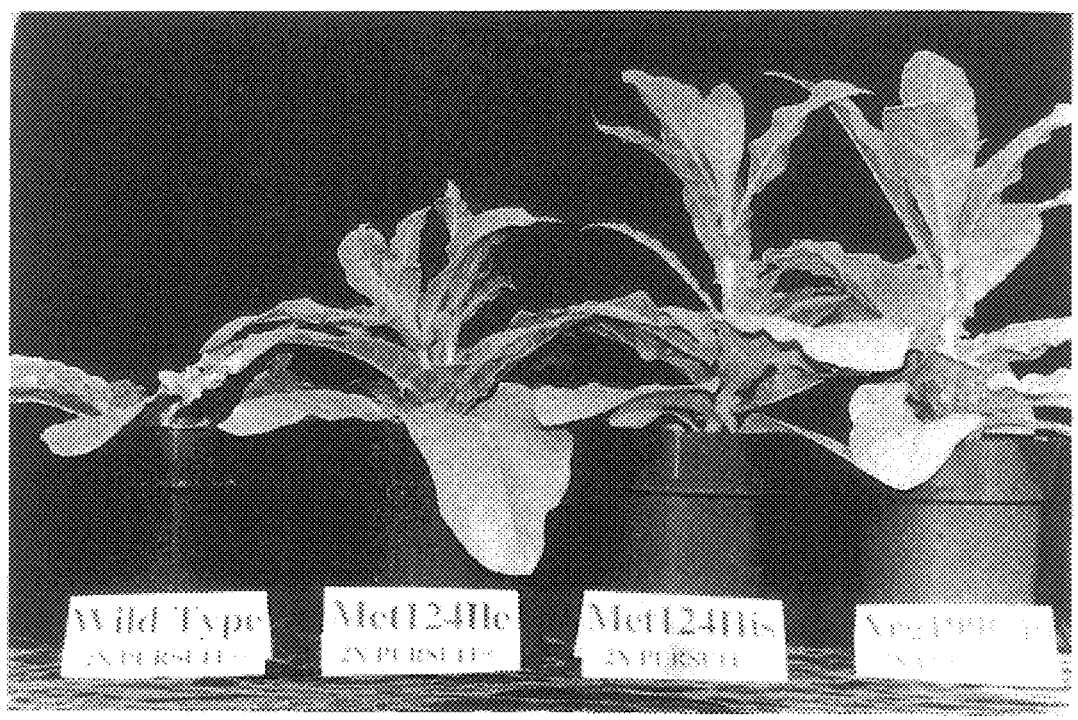
FIG. 14 is a photograph showing tobacco plants transformed with the Arabidopsis AHAS gene containing either the Met124Ile, Met 124His, or Arg199Glu mutation and a non-transformed control, which had been sprayed with twice the field rate (100 g/ha) of imazethapyr.

Kanamycin-resistant tobacco shoots were transferred to medium containing a 0.25 $\mu$M imazethapyr. At this concentration of the imidazolinone herbicide, non-transformed tobacco shoots (containing endogenous wild-type AHAS) were not able to initiate root formation. By contrast, root initiation and growth were observed from tobacco shoots transformed with each of the mutant AHAS genes. Roots developed from shoots transformed with the Met124Ile and Arg199Glu mutant genes along with wild type are shown in FIG. 1. Furthermore, plants transformed with the Met124Ile or Arg199Glu mutant genes were resistant to spraying with twice the field rate (100 g/ha) of imazethapyr (FIG. 13). The patterns of root growth in transformed vs. non-transformed plants in the presence of herbicide, as well as the behavior after herbicide spraying suggest that expression of the rationally designed herbicide resistance genes confers herbicide resistance in vivo.

Detection of the Rationally Designed Genes in Herbicide Resistant Tobacco

Genomic DNA was isolated from the AHAS-transformed tobacco plants, and the presence of the Arabidopsis AHAS variant genes was verified by PCR analysis. Differences between the nucleotide sequences of the Arabidopsis AHAS gene and the two tobacco AHAS genes were exploited to design PCR primers that amplify only the Arabidopsis gene in a tobacco genomic DNA background. The rationally designed herbicide resistance genes were detected, as shown by amplification of a DNA fragment of the proper size, in a majority of the herbicide resistant plants. No PCR signal was seen from non-transformed tobacco plants.

Segregation of Transformed AHAS Genes:

To monitor segregation of rationally designed AHAS genes in transformed plants, germination tests were performed. Seeds were placed in hormone-free Murashige-Skoog medium containing up to 2.5 µM PURSUIT® and 100 µM kanamycin. The seedlings that resulted were visually scored for resistance or susceptibility to the herbicide.

Since tobacco plants are diploid, it would be expected that the progeny of self-pollinated plants should segregate 3:1 resistant:susceptible, reflecting the existence of 1 seedling homozygous for the resistant AHAS gene, 2 seedlings heterozygous for the resistant AHAS gene, and 1 seedling lacking a resistant AHAS gene.

The results indicate that resistant AHAS genes are segregating in the expected 3:1 ratio, supporting the conclusion that herbicide resistance is conferred by a single, dominant copy of a rationally designed AHAS gene.

These results indicate that rational design of herbicide-resistant AHAS genes can be used to produce plants that exhibit herbicide resistant growth in vivo.

EXAMPLE 9

Figure 15:
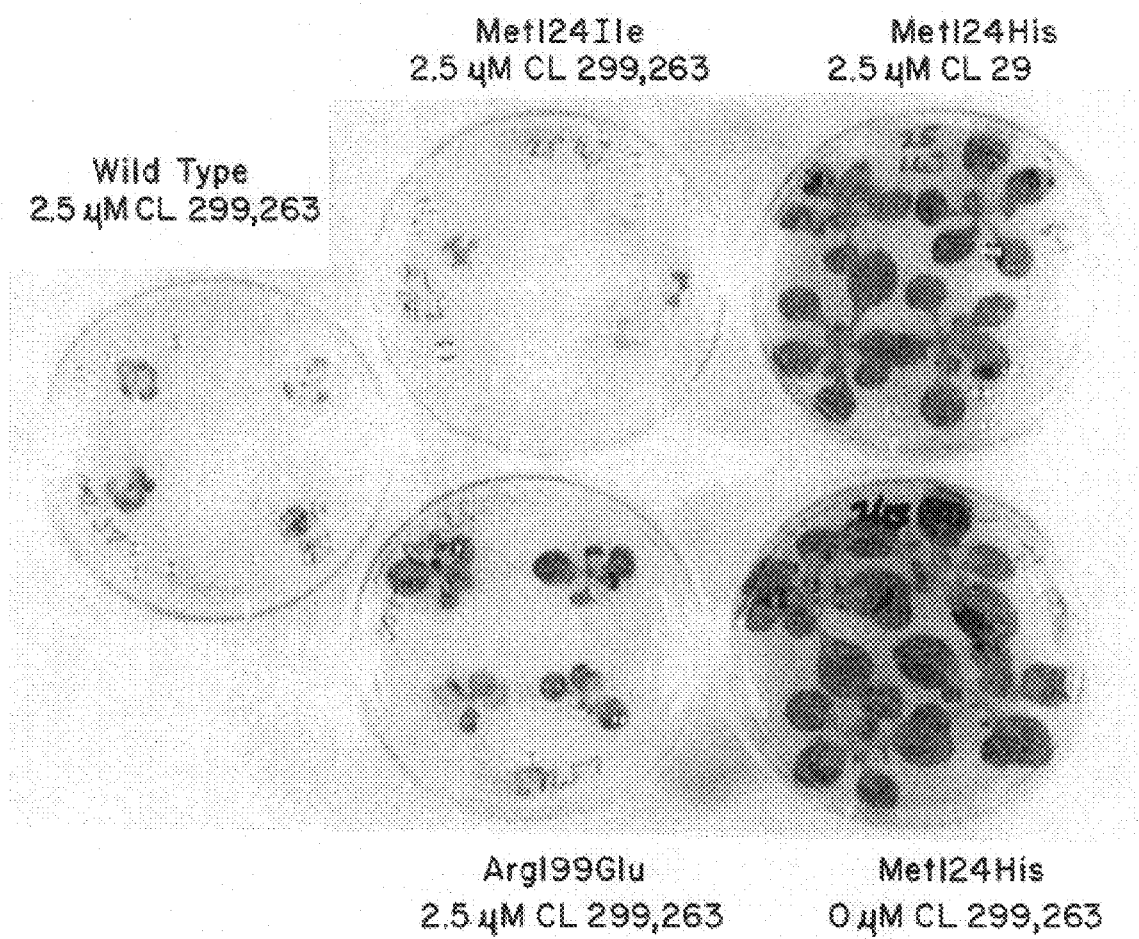
FIG. 15 is a photograph showing the results of germination tests performed in the presence of the herbicide CL 299,263 (imazamox), which were performed on seeds harvested from primary tobacco plant transformants that had been transformed with the Arabidopsis AHAS gene containing either the Met124Ile, Met 124His, or Arg199Glu mutation.

Production of Plants Cross-Resistant to Different Herbicides by Transformation with Rationally Designed AHAS Genes Tobacco plants transformed with rationally designed AHAS genes as described in Example 8 above were also tested for cross-resistance to another herbicide, CL 299,263 (also known as imazamox). Germination tests were performed on seeds harvested from the primary transformants containing the Met124Ile, Met124His, and Arg199Glu Arabidopsis AHAS variant genes, in the absence or presence of 2.5 µM CL 299,263 (FIG. 15). This concentration of the herbicide causes severe stunting and bleaching of wild-type tobacco plants. Tobacco plants transformed with the Met124His AHAS gene showed the greatest level of resistance (FIG. 15). Arg199Glu transformants showed an intermediate level of resistance, while Met124Ile showed little resistance (FIG. 15).

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A variant plant acetohydroxy acid synthase (AHAS) protein comprising at least one mutation at an amino acid residue corresponding to an amino acid residue selected from the group consisting of M53, R128, I330, and any combination of the foregoing, of SEQ ID NO:1, where said variant plant AHAS protein is more resistant to an herbicide than a wild-type AHAS protein.

2. A variant AHAS protein as defined in claim 1, wherein said herbicide is selected from the group consisting of an imidazolinones, sulfonylureas, triazolopyrimidine, sulfomamides, pyrimidyl-oxy-benzoic acids, sulfamoylureas, sulfonylcarboxamides, and combinations thereof.

3. A variant AHAS protein as defined in claim 1, wherein said AHAS protein is derived from *Arabidopsis thaliana*.

4. A variant AHAS protein as defined in claim 1, wherein said substitution is selected from the group consisting of Met53Trp, Met53Glu, Met53Ile, Met53His, Arg128Ala, Arg128Glu, Ile330Phe, an identical substitution at an amino acid residue of another plant AHAS protein at an amino acid position aligned with any of the foregoing, or a combination of any of the foregoing.

5. A variant AHAS protein as defined in claim 1, wherein said variant AHAS protein has catalytic activity that is more resistant to at least one herbicide than is wild type AHAS.

6. A variant AHAS protein as defined in claim 1, wherein said variant AHAS has more than about 20% of the catalytic activity of wild-type AHAS.

7. A variant AHAS protein as defined in claim 1, wherein said variant AHAS is at least 2-fold more resistant to imidazolinone-based herbicides than to sulfonylurea-based herbicides.

* * * * *

SEQUENCE LISTING

<160> NUMBER OF SEQ ID NOS: 9

<210> SEQ ID NO 1
<211> LENGTH: 599
<212> TYPE: PRT
<213> ORGANISM: Zea Mays

<400> SEQUENCE: 1

```
Gly Ser Ala Ala Ser Pro Ala Met Pro Met Ala Pro Pro Ala Thr Pro
1               5                   10                  15

Leu Arg Pro Trp Gly Pro Thr Asp Pro Arg Lys Gly Ala Asp Ile Leu
            20                  25                  30

Val Glu Ser Leu Glu Arg Cys Gly Val Arg Asp Val Phe Ala Tyr Pro
        35                  40                  45

Gly Gly Ala Ser Met Glu Ile His Gln Ala Leu Thr Arg Ser Pro Val
    50                  55                  60

Ile Ala Asn His Leu Phe Arg His Glu Gln Gly Glu Ala Phe Ala Ala
65                  70                  75                  80

Ser Gly Tyr Ala Arg Ser Ser Gly Arg Val Gly Val Cys Ile Ala Thr
            85                  90                  95

Ser Gly Pro Gly Ala Thr Asn Leu Val Ser Ala Leu Ala Asp Ala Leu
            100                 105                 110

Leu Asp Ser Val Pro Met Val Ala Ile Thr Gly Gln Val Pro Arg Arg
            115                 120                 125

Met Ile Gly Thr Asp Ala Phe Gln Glu Thr Pro Ile Val Glu Val Thr
    130                 135                 140

Arg Ser Ile Thr Lys His Asn Tyr Leu Val Leu Asp Val Asp Asp Ile
145                 150                 155                 160

Pro Arg Val Val Gln Glu Ala Phe Phe Leu Ala Ser Ser Gly Arg Pro
```

```
                165                 170                 175
Gly Pro Val Leu Val Asp Ile Pro Lys Asp Ile Gln Gln Met Ala
                180                 185                 190

Val Pro Val Trp Asp Lys Pro Met Ser Leu Pro Gly Tyr Ile Ala Arg
            195                 200                 205

Leu Pro Lys Pro Pro Ala Thr Glu Leu Leu Glu Gln Val Leu Arg Leu
        210                 215                 220

Val Gly Glu Ser Arg Arg Pro Val Leu Tyr Val Gly Gly Cys Ala
225                 230                 235                 240

Arg Ser Gly Glu Glu Leu Arg Arg Phe Val Glu Leu Thr Gly Ile Pro
                245                 250                 255

Val Thr Thr Thr Leu Met Gly Leu Gly Asn Phe Pro Ser Asp Asp Pro
            260                 265                 270

Leu Ser Leu Arg Met Leu Gly Met His Gly Thr Val Tyr Ala Asn Tyr
        275                 280                 285

Ala Val Asp Lys Ala Asp Leu Leu Ala Leu Gly Val Arg Phe Asp
    290                 295                 300

Asp Arg Val Thr Gly Lys Ile Glu Ala Phe Ala Ser Arg Ala Lys Ile
305                 310                 315                 320

Val His Val Asp Ile Asp Pro Ala Glu Ile Gly Lys Asn Lys Gln Pro
                325                 330                 335

His Val Ser Ile Cys Ala Asp Val Lys Leu Ala Leu Gln Gly Met Asn
            340                 345                 350

Ala Leu Leu Glu Gly Ser Thr Ser Lys Lys Ser Phe Asp Phe Gly Ser
        355                 360                 365

Trp Asn Asp Glu Leu Asp Gln Gln Lys Arg Glu Phe Pro Leu Gly Tyr
    370                 375                 380

Lys Tyr Ser Asn Glu Glu Ile Gln Pro Gln Tyr Ala Ile Gln Val Leu
385                 390                 395                 400

Asp Glu Leu Thr Lys Gly Glu Ala Ile Ile Gly Thr Gly Val Gly Gln
            405                 410                 415

His Gln Met Trp Ala Ala Gln Tyr Tyr Thr Tyr Lys Arg Pro Arg Gln
        420                 425                 430

Trp Leu Ser Ser Ala Gly Leu Gly Ala Met Gly Phe Gly Leu Pro Ala
    435                 440                 445

Ala Ala Gly Ala Ser Val Ala Asn Pro Gly Val Thr Val Val Asp Ile
450                 455                 460

Asp Gly Asp Gly Ser Phe Leu Met Asn Val Gln Glu Leu Ala Met Ile
465                 470                 475                 480

Arg Ile Glu Asn Leu Pro Val Lys Val Phe Val Leu Asn Asn Gln His
            485                 490                 495

Leu Gly Met Val Val Gln Trp Glu Asp Arg Phe Tyr Lys Ala Asn Arg
        500                 505                 510

Ala His Thr Tyr Leu Gly Asn Pro Glu Asn Glu Ser Glu Ile Tyr Pro
    515                 520                 525

Asp Phe Val Thr Ile Ala Lys Gly Phe Asn Ile Pro Ala Val Arg Val
    530                 535                 540

Thr Lys Lys Asn Glu Val Arg Ala Ala Ile Lys Lys Met Leu Glu Thr
545                 550                 555                 560

Pro Gly Pro Tyr Leu Leu Asp Ile Ile Val Pro His Gln Glu His Val
                565                 570                 575

Leu Pro Met Ile Pro Ser Gly Gly Ala Phe Lys Asp Met Ile Leu Asp
            580                 585                 590
```

-continued

```
Gly Asp Gly Arg Thr Val Tyr
            595

<210> SEQ ID NO 2
<211> LENGTH: 585
<212> TYPE: PRT
<213> ORGANISM: Lactobacillus planarum

<400> SEQUENCE: 2

Thr Asn Ile Leu Ala Gly Ala Val Ile Lys Val Leu Glu Ala Trp
 1               5                  10                  15

Gly Val Asp His Leu Tyr Gly Ile Pro Gly Gly Ser Ile Asn Ser Ile
                20                  25                  30

Met Asp Ala Leu Ser Ala Glu Arg Asp Arg Ile His Tyr Ile Gln Val
            35                  40                  45

Arg His Glu Glu Val Gly Ala Met Ala Ala Ala Asp Ala Lys Leu
50                  55                  60

Thr Gly Lys Ile Gly Val Cys Phe Gly Ser Ala Gly Pro Gly Gly Thr
65                  70                  75                  80

His Leu Met Asn Gly Leu Tyr Asp Ala Arg Glu Asp His Val Pro Val
                85                  90                  95

Leu Ala Leu Ile Gly Gln Phe Gly Thr Thr Gly Met Asn Met Asp Thr
            100                 105                 110

Phe Gln Glu Met Asn Glu Asn Pro Ile Tyr Ala Asp Val Ala Asp Tyr
        115                 120                 125

Asn Val Thr Ala Val Asn Ala Ala Thr Leu Pro His Val Ile Asp Glu
    130                 135                 140

Ala Ile Arg Arg Ala Tyr Ala His Gln Gly Val Ala Val Val Gln Ile
145                 150                 155                 160

Pro Val Asp Leu Pro Trp Gln Gln Ile Ser Ala Glu Asp Trp Tyr Ala
                165                 170                 175

Ser Ala Asn Asn Tyr Gln Thr Pro Leu Leu Pro Glu Pro Asp Val Gln
            180                 185                 190

Ala Val Thr Arg Leu Thr Gln Thr Leu Leu Ala Ala Glu Arg Pro Leu
        195                 200                 205

Ile Tyr Tyr Gly Ile Gly Ala Arg Lys Ala Gly Lys Glu Leu Glu Gln
    210                 215                 220

Leu Ser Lys Thr Leu Lys Ile Pro Leu Met Ser Thr Tyr Pro Ala Lys
225                 230                 235                 240

Gly Ile Val Ala Asp Arg Tyr Pro Ala Tyr Leu Gly Ser Ala Asn Arg
                245                 250                 255

Val Ala Gln Lys Pro Ala Asn Glu Ala Leu Ala Gln Ala Asp Val Val
            260                 265                 270

Leu Phe Val Gly Asn Asn Tyr Pro Phe Ala Glu Val Ser Lys Ala Phe
        275                 280                 285

Lys Asn Thr Arg Tyr Phe Leu Gln Ile Asp Ile Asp Pro Ala Lys Leu
    290                 295                 300

Gly Lys Arg His Lys Thr Asp Ile Ala Val Leu Ala Asp Ala Gln Lys
305                 310                 315                 320

Thr Leu Ala Ala Ile Leu Ala Gln Val Ser Glu Arg Glu Ser Thr Pro
                325                 330                 335

Trp Trp Gln Ala Asn Leu Ala Asn Val Lys Asn Trp Arg Ala Tyr Leu
            340                 345                 350

Ala Ser Leu Glu Asp Lys Gln Glu Gly Pro Leu Gln Ala Tyr Gln Val
```

-continued

```
            355                 360                 365
Leu Arg Ala Val Asn Lys Ile Ala Glu Pro Asp Ala Ile Tyr Ser Ile
    370                 375                 380

Asp Val Gly Asp Ile Asn Leu Asn Ala Asn Arg His Leu Lys Leu Thr
385                 390                 395                 400

Pro Ser Asn Arg His Ile Thr Ser Asn Leu Phe Ala Thr Met Gly Val
                405                 410                 415

Gly Ile Pro Gly Ala Ile Ala Ala Lys Leu Asn Tyr Pro Glu Arg Gln
            420                 425                 430

Val Phe Asn Leu Ala Gly Asp Gly Ala Ser Met Thr Met Gln Asp
        435                 440                 445

Leu Val Thr Gln Val Gln Tyr His Leu Pro Val Ile Asn Val Val Phe
    450                 455                 460

Thr Asn Cys Gln Tyr Gly Phe Ile Lys Asp Glu Gln Glu Asp Thr Asn
465                 470                 475                 480

Gln Asn Asp Phe Ile Gly Val Glu Phe Asn Asp Ile Asp Phe Ser Lys
                485                 490                 495

Ile Ala Asp Gly Val His Met Gln Ala Phe Arg Val Asn Lys Ile Glu
            500                 505                 510

Gln Leu Pro Asp Val Phe Glu Gln Ala Lys Ala Ile Ala Gln His Glu
        515                 520                 525

Pro Val Leu Ile Asp Ala Val Ile Thr Gly Asp Arg Pro Leu Pro Ala
530                 535                 540

Glu Lys Leu Arg Leu Asp Ser Ala Met Ser Ser Ala Ala Asp Ile Glu
545                 550                 555                 560

Ala Phe Lys Gln Arg Tyr Glu Ala Gln Asp Leu Gln Pro Leu Ser Thr
                565                 570                 575

Tyr Leu Lys Gln Phe Gly Leu Asp Asp
            580                 585

<210> SEQ ID NO 3
<211> LENGTH: 638
<212> TYPE: PRT
<213> ORGANISM: Zea Mays

<400> SEQUENCE: 3

Met Ala Thr Ala Ala Ala Ser Thr Ala Leu Thr Gly Ala Thr Thr
  1               5                  10                  15

Ala Ala Pro Lys Ala Arg Arg Ala His Leu Leu Ala Thr Arg Arg
                20                  25                  30

Ala Leu Ala Ala Pro Ile Arg Cys Ser Ala Ala Ser Pro Ala Met Pro
            35                  40                  45

Met Ala Pro Pro Ala Thr Pro Leu Arg Pro Trp Gly Pro Thr Asp Pro
    50                  55                  60

Arg Lys Gly Ala Asp Ile Leu Val Glu Ser Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Gly Tyr Ala Arg Ser Ser Gly Arg
        115                 120                 125

Val Gly Val Cys Ile Ala Thr Ser Gly Pro Gly Ala Thr Asn Leu Val
    130                 135                 140
```

```
Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
            165                 170                 175

Thr Pro Ile Val Glu Val Thr Arg Ser Ile Thr Lys His Asn Tyr Leu
            180                 185                 190

Val Leu Asp Val Asp Asp Ile Pro Arg Val Val Gln Glu Ala Phe Phe
        195                 200                 205

Leu Ala Ser Ser Gly Arg Pro Gly Pro Val Leu Val Asp Ile Pro Lys
    210                 215                 220

Asp Ile Gln Gln Gln Met Ala Val Pro Val Trp Asp Lys Pro Met Ser
225                 230                 235                 240

Leu Pro Gly Tyr Ile Ala Arg Leu Pro Lys Pro Pro Ala Thr Glu Leu
                245                 250                 255

Leu Glu Gln Val Leu Arg Leu Val Gly Glu Ser Arg Arg Pro Val Leu
            260                 265                 270

Tyr Val Gly Gly Gly Cys Ala Ala Ser Gly Glu Glu Leu Arg Arg Phe
            275                 280                 285

Val Glu Leu Thr Gly Ile Pro Val Thr Thr Thr Leu Met Gly Leu Gly
        290                 295                 300

Asn Phe Pro Ser Asp Asp Pro Leu Ser Leu Arg Met Leu Gly Met His
305                 310                 315                 320

Gly Thr Val Tyr Ala Asn Tyr Ala Val Asp Lys Ala Asp Leu Leu Leu
                325                 330                 335

Ala Leu Gly Val Arg Phe Asp Asp Arg Val Thr Gly Lys Ile Glu Ala
            340                 345                 350

Phe Ala Ser Arg Ala Lys Ile Val His Val Asp Ile Asp Pro Ala Glu
            355                 360                 365

Ile Gly Lys Asn Lys Gln Pro His Val Ser Ile Cys Ala Asp Val Lys
        370                 375                 380

Leu Ala Leu Gln Gly Met Asn Ala Leu Leu Glu Gly Ser Thr Ser Lys
385                 390                 395                 400

Lys Ser Phe Asp Phe Gly Ser Trp Asn Asp Glu Leu Asp Gln Gln Lys
                405                 410                 415

Arg Glu Phe Pro Leu Gly Tyr Lys Thr Ser Asn Glu Glu Ile Gln Pro
            420                 425                 430

Gln Tyr Ala Ile Gln Val Leu Asp Glu Leu Thr Lys Gly Glu Ala Ile
        435                 440                 445

Ile Gly Thr Gly Val Gly Gln His Gln Met Trp Ala Ala Gln Tyr Tyr
    450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Ser Val Ala Asn Pro
                485                 490                 495

Gly Val Thr Val Val Asp Ile Asp Gly Asp Gly Ser Phe Leu Met Asn
            500                 505                 510

Val Gln Glu Leu Ala Met Ile Arg Ile Glu Asn Leu Pro Val Lys Val
        515                 520                 525

Phe Val Leu Asn Asn Gln His Leu Gly Met Val Val Gln Trp Glu Asp
    530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
```

```
                        565                 570                 575
Asn Ile Pro Ala Val Arg Val Thr Lys Lys Asn Glu Val Arg Ala Ala
                580                 585                 590

Ile Lys Lys Met Leu Glu Thr Pro Gly Pro Tyr Leu Leu Asp Ile Ile
            595                 600                 605

Val Pro His Gln Glu His Val Leu Pro Met Ile Pro Ser Gly Gly Ala
        610                 615                 620

Phe Lys Asp Met Ile Leu Asp Gly Asp Gly Arg Thr Val Tyr
625                 630                 635

<210> SEQ ID NO 4
<211> LENGTH: 638
<212> TYPE: PRT
<213> ORGANISM: Zea Mays

<400> SEQUENCE: 4

Met Ala Thr Ala Ala Thr Ala Ala Ala Leu Thr Gly Ala Thr Thr
1               5                   10                  15

Ala Thr Pro Lys Ser Arg Arg Ala His His Leu Ala Thr Arg Arg
            20                  25                  30

Ala Leu Ala Ala Pro Ile Arg Cys Ser Ala Leu Ser Arg Ala Thr Pro
        35                  40                  45

Thr Ala Pro Pro Ala Thr Pro Leu Arg Pro Trp Gly Pro Asn Glu Pro
    50                  55                  60

Arg Lys Gly Ser Asp Ile Leu Val Glu Ala Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Ala Tyr Ala Arg Ser Ser Gly Arg
        115                 120                 125

Val Gly Val Cys Ile Ala Thr Ser Gly Pro Gly Ala Thr Asn Leu Val
    130                 135                 140

Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
            180                 185                 190

Val Leu Asp Val Asp Asp Ile Pro Arg Val Val Gln Glu Ala Phe Phe
        195                 200                 205

Leu Ala Ser Ser Gly Arg Pro Gly Pro Val Leu Val Asp Ile Pro Lys
    210                 215                 220

Asp Ile Gln Gln Gln Met Ala Val Pro Ala Trp Asp Thr Pro Met Ser
225                 230                 235                 240

Leu Pro Gly Tyr Ile Ala Arg Leu Pro Lys Pro Pro Ala Thr Glu Phe
                245                 250                 255

Leu Glu Gln Val Leu Arg Leu Val Gly Glu Ser Arg Arg Pro Val Leu
            260                 265                 270

Tyr Val Gly Gly Gly Cys Ala Ala Ser Gly Glu Glu Leu Cys Arg Phe
        275                 280                 285

Val Glu Leu Thr Gly Ile Pro Val Thr Thr Thr Leu Met Gly Leu Gly
    290                 295                 300
```

-continued

```
Asn Phe Pro Ser Asp Asp Pro Leu Ser Leu Arg Met Leu Gly Met His
305                 310                 315                 320

Gly Thr Val Tyr Ala Asn Tyr Ala Val Asp Lys Ala Asp Leu Leu Leu
                325                 330                 335

Ala Phe Gly Val Arg Phe Asp Asp Arg Val Thr Gly Lys Ile Glu Ala
                340                 345                 350

Phe Ala Gly Arg Ala Lys Ile Val His Ile Asp Ile Asp Pro Ala Glu
                355                 360                 365

Ile Gly Lys Asn Lys Gln Pro His Val Ser Ile Cys Ala Asp Val Lys
        370                 375                 380

Leu Ala Leu Gln Gly Met Asn Thr Leu Leu Glu Gly Ser Thr Ser Lys
385                 390                 395                 400

Lys Ser Phe Asp Phe Gly Ser Trp His Asp Glu Leu Asp Gln Gln Lys
                405                 410                 415

Arg Glu Phe Pro Leu Gly Tyr Lys Ile Phe Asn Glu Glu Ile Gln Pro
                420                 425                 430

Gln Tyr Ala Ile Gln Val Leu Asp Glu Leu Thr Lys Gly Glu Ala Ile
                435                 440                 445

Ile Ala Thr Gly Val Gly Gln His Gln Met Trp Ala Ala Gln Tyr Tyr
        450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Ala Val Ala Asn Pro
                485                 490                 495

Gly Val Thr Val Val Asp Ile Asp Gly Asp Gly Ser Phe Leu Met Asn
                500                 505                 510

Ile Gln Glu Leu Ala Met Ile Arg Ile Glu Asn Leu Pro Val Lys Val
        515                 520                 525

Phe Val Leu Asn Asn Gln His Leu Gly Met Val Val Gln Trp Glu Asp
530                 535                 540

Arg Phe Tyr Lys Ala Asn Arg Ala His Thr Phe Leu Gly Asn Pro Glu
545                 550                 555                 560

Asn Glu Ser Glu Ile Tyr Pro Asp Phe Val Ala Ile Ala Lys Gly Phe
                565                 570                 575

Asn Ile Pro Ala Val Arg Val Thr Lys Lys Ser Glu Val His Ala Ala
                580                 585                 590

Ile Lys Lys Met Leu Glu Ala Pro Gly Pro Tyr Leu Leu Asp Ile Ile
        595                 600                 605

Val Pro His Gln Glu His Val Leu Pro Met Ile Pro Ser Gly Gly Ala
        610                 615                 620

Phe Lys Asp Met Ile Leu Asp Gly Asp Gly Arg Thr Val Tyr
625                 630                 635
```

<210> SEQ ID NO 5
<211> LENGTH: 667
<212> TYPE: PRT
<213> ORGANISM: Tobacco

<400> SEQUENCE: 5

```
Met Ala Ala Ala Pro Ser Pro Ser Ser Ala Phe Ser Lys Thr
 1               5                  10                  15

Leu Ser Pro Ser Ser Thr Ser Ser Thr Leu Leu Pro Arg Ser Thr
                20                  25                  30

Phe Pro Phe Pro His His Pro His Lys Thr Thr Pro Pro Leu His
                35                  40                  45
```

```
Leu Thr His Thr His Ile His Ile His Ser Gln Arg Arg Phe Thr
 50                  55                  60

Ile Ser Asn Val Ile Ser Thr Asn Gln Lys Val Ser Gln Thr Glu Lys
 65                  70                  75                  80

Thr Glu Thr Phe Val Ser Arg Phe Ala Pro Asp Glu Pro Arg Lys Gly
                 85                  90                  95

Ser Asp Val Leu Val Glu Ala Leu Glu Arg Glu Gly Val Thr Asp Val
                100                 105                 110

Phe Ala Tyr Pro Gly Gly Ala Ser Met Glu Ile His Gln Ala Leu Thr
                115                 120                 125

Arg Ser Ser Ile Ile Arg Asn Val Leu Pro Arg His Glu Gln Gly Gly
                130                 135                 140

Val Phe Ala Ala Glu Gly Tyr Ala Arg Ala Thr Gly Phe Pro Gly Val
145                 150                 155                 160

Cys Ile Ala Thr Ser Gly Pro Gly Ala Thr Asn Leu Val Ser Gly Leu
                165                 170                 175

Ala Asp Ala Leu Leu Asp Ser Val Pro Ile Val Ala Ile Thr Gly Gln
                180                 185                 190

Val Pro Arg Arg Met Ile Gly Thr Asp Ala Phe Gln Glu Thr Pro Ile
                195                 200                 205

Val Glu Val Thr Arg Ser Ile Thr Lys His Asn Tyr Leu Val Met Asp
210                 215                 220

Val Glu Asp Ile Pro Arg Val Arg Glu Ala Phe Phe Leu Ala Arg
225                 230                 235                 240

Ser Gly Arg Pro Gly Pro Ile Leu Ile Asp Val Pro Lys Asp Ile Gln
                245                 250                 255

Gln Gln Leu Val Ile Pro Asp Trp Asp Gln Pro Met Arg Leu Pro Gly
                260                 265                 270

Tyr Met Ser Arg Leu Pro Lys Leu Pro Asn Glu Met Leu Leu Glu Gln
                275                 280                 285

Ile Val Arg Leu Ile Ser Glu Ser Lys Lys Pro Val Leu Tyr Val Gly
                290                 295                 300

Gly Gly Cys Ser Gln Ser Ser Glu Asp Leu Arg Arg Phe Val Glu Leu
305                 310                 315                 320

Thr Gly Ile Pro Val Ala Ser Thr Leu Met Gly Leu Gly Ala Phe Pro
                325                 330                 335

Thr Gly Asp Glu Leu Ser Leu Ser Met Leu Gly Met His Gly Thr Val
                340                 345                 350

Tyr Ala Asn Tyr Ala Val Asp Ser Ser Asp Leu Leu Leu Ala Phe Gly
                355                 360                 365

Val Arg Phe Asp Asp Arg Val Thr Gly Lys Leu Glu Ala Phe Ala Ser
                370                 375                 380

Arg Ala Lys Ile Val His Ile Asp Ile Asp Ser Ala Glu Ile Gly Lys
385                 390                 395                 400

Asn Lys Gln Pro His Val Ser Ile Cys Ala Asp Ile Lys Leu Ala Leu
                405                 410                 415

Gln Gly Leu Asn Ser Ile Leu Glu Ser Lys Glu Gly Lys Leu Lys Leu
                420                 425                 430

Asp Phe Ser Ala Trp Arg Gln Glu Leu Thr Glu Gln Lys Val Lys His
                435                 440                 445

Pro Leu Asn Phe Lys Thr Phe Gly Asp Ala Ile Pro Pro Gln Tyr Ala
                450                 455                 460
```

-continued

```
Ile Gln Val Leu Asp Glu Leu Thr Asn Gly Asn Ala Ile Ile Ser Thr
465                 470                 475                 480

Gly Val Gly Gln His Gln Met Trp Ala Ala Gln Tyr Tyr Lys Tyr Arg
                485                 490                 495

Lys Pro Arg Gln Trp Leu Thr Ser Gly Leu Gly Ala Met Gly Phe
            500                 505                 510

Gly Leu Pro Ala Ala Ile Gly Ala Ala Val Gly Arg Pro Asp Glu Val
            515                 520                 525

Val Val Asp Ile Asp Gly Asp Gly Ser Phe Ile Met Asn Val Gln Glu
530                 535                 540

Leu Ala Thr Ile Lys Val Glu Asn Leu Pro Val Lys Ile Met Leu Leu
545                 550                 555                 560

Asn Asn Gln His Leu Gly Met Val Val Gln Trp Glu Asp Arg Phe Tyr
                565                 570                 575

Lys Ala Asn Arg Ala His Thr Tyr Leu Gly Asn Pro Ser Asn Glu Ala
            580                 585                 590

Glu Ile Phe Pro Asn Met Leu Lys Phe Ala Glu Ala Cys Gly Val Pro
            595                 600                 605

Ala Ala Arg Val Thr His Arg Asp Leu Arg Ala Ala Ile Gln Lys
610                 615                 620

Met Leu Asp Thr Pro Gly Pro Tyr Leu Leu Asp Val Ile Val Pro His
625                 630                 635                 640

Gln Glu His Val Leu Pro Met Ile Pro Ser Gly Gly Ala Phe Lys Asp
                645                 650                 655

Val Ile Thr Glu Gly Asp Gly Arg Ser Ser Tyr
            660                 665
```

<210> SEQ ID NO 6
<211> LENGTH: 664
<212> TYPE: PRT
<213> ORGANISM: Tobacco

<400> SEQUENCE: 6

```
Met Ala Ala Ala Ala Ala Pro Ser Pro Ser Phe Ser Lys Thr Leu
 1               5                  10                  15

Ser Ser Ser Ser Ser Lys Ser Ser Thr Leu Leu Pro Arg Ser Thr Phe
                20                  25                  30

Pro Phe Pro His His Pro His Lys Thr Thr Pro Pro Leu His Leu
            35                  40                  45

Thr Pro Thr His Ile His Ser Gln Arg Arg Phe Thr Ile Ser Asn
    50                  55                  60

Val Ile Ser Thr Thr Gln Lys Val Ser Glu Thr Gln Lys Ala Glu Thr
 65                  70                  75                  80

Phe Val Ser Arg Phe Ala Pro Asp Glu Pro Arg Lys Gly Ser Asp Val
                85                  90                  95

Leu Val Glu Ala Leu Glu Arg Glu Gly Val Thr Asp Val Phe Ala Tyr
            100                 105                 110

Pro Gly Gly Ala Ser Met Glu Ile His Gln Ala Leu Thr Arg Ser Ser
        115                 120                 125

Ile Ile Arg Asn Val Leu Pro Arg His Glu Gln Gly Gly Val Phe Ala
    130                 135                 140

Ala Glu Gly Tyr Ala Arg Ala Thr Gly Phe Pro Gly Val Cys Ile Ala
145                 150                 155                 160

Thr Ser Gly Pro Gly Ala Thr Asn Leu Val Ser Gly Leu Ala Asp Ala
                165                 170                 175
```

-continued

```
Leu Leu Asp Ser Val Pro Ile Val Ala Ile Thr Gly Gln Val Pro Arg
        180                 185                 190
Arg Met Ile Gly Thr Asp Ala Phe Gln Glu Thr Pro Ile Val Glu Val
            195                 200                 205
Thr Arg Ser Ile Thr Lys His Asn Tyr Leu Val Met Asp Val Glu Asp
        210                 215                 220
Ile Pro Arg Val Val Arg Glu Ala Phe Phe Leu Ala Arg Ser Gly Arg
225                 230                 235                 240
Pro Gly Pro Val Leu Ile Asp Val Pro Lys Asp Ile Gln Gln Gln Leu
                245                 250                 255
Val Ile Pro Asp Trp Asp Gln Pro Met Arg Leu Pro Gly Tyr Met Ser
            260                 265                 270
Arg Leu Pro Lys Leu Pro Asn Glu Met Leu Leu Glu Gln Ile Val Arg
        275                 280                 285
Leu Ile Ser Glu Ser Lys Lys Pro Val Leu Tyr Val Gly Gly Gly Cys
        290                 295                 300
Ser Gln Ser Ser Glu Glu Leu Arg Arg Phe Val Glu Leu Thr Gly Ile
305                 310                 315                 320
Pro Val Ala Ser Thr Leu Met Gly Leu Gly Ala Phe Pro Thr Gly Asp
                325                 330                 335
Glu Leu Ser Leu Ser Met Leu Gly Met His Gly Thr Val Tyr Ala Asn
            340                 345                 350
Tyr Ala Val Asp Ser Ser Asp Leu Leu Leu Ala Phe Gly Val Arg Phe
        355                 360                 365
Asp Asp Arg Val Thr Gly Lys Leu Glu Ala Phe Ala Ser Arg Ala Lys
        370                 375                 380
Ile Val His Ile Asp Ile Asp Ser Ala Glu Ile Gly Lys Asn Lys Gln
385                 390                 395                 400
Pro His Val Ser Ile Cys Ala Asp Ile Lys Leu Ala Leu Gln Gly Leu
                405                 410                 415
Asn Ser Ile Leu Glu Ser Lys Glu Gly Lys Leu Lys Leu Asp Phe Ser
            420                 425                 430
Ala Trp Arg Gln Glu Leu Thr Val Gln Lys Val Lys Tyr Pro Leu Asn
        435                 440                 445
Phe Lys Thr Phe Gly Asp Ala Ile Pro Pro Gln Tyr Ala Ile Gln Val
        450                 455                 460
Leu Asp Glu Leu Thr Asn Gly Ser Ala Ile Ile Ser Thr Gly Val Gly
465                 470                 475                 480
Gln His Gln Met Trp Ala Ala Gln Tyr Tyr Lys Tyr Arg Lys Pro Arg
                485                 490                 495
Gln Trp Leu Thr Ser Gly Gly Leu Gly Ala Met Gly Phe Gly Leu Pro
            500                 505                 510
Ala Ala Ile Gly Ala Ala Val Gly Arg Pro Asp Glu Val Val Val Asp
        515                 520                 525
Ile Asp Gly Asp Gly Ser Phe Ile Met Asn Val Gln Glu Leu Ala Thr
        530                 535                 540
Ile Lys Val Glu Asn Leu Pro Val Lys Ile Met Leu Leu Asn Asn Gln
545                 550                 555                 560
His Leu Gly Met Val Val Gln Trp Glu Asp Arg Phe Tyr Lys Ala Asn
                565                 570                 575
Arg Ala His Thr Tyr Leu Gly Asn Pro Ser Asn Glu Ala Glu Ile Phe
            580                 585                 590
```

```
Pro Asn Met Leu Lys Phe Ala Glu Ala Cys Gly Val Pro Ala Ala Arg
            595                 600                 605

Val Thr His Arg Asp Asp Leu Arg Ala Ala Ile Gln Lys Met Leu Asp
        610                 615                 620

Thr Pro Gly Pro Tyr Leu Leu Asp Val Ile Val Pro His Gln Glu His
625                 630                 635                 640

Val Leu Pro Met Ile Pro Ser Gly Gly Ala Phe Lys Asp Val Ile Thr
                645                 650                 655

Glu Gly Asp Gly Arg Ser Ser Tyr
                660

<210> SEQ ID NO 7
<211> LENGTH: 671
<212> TYPE: PRT
<213> ORGANISM: Arabidopsis thaliana

<400> SEQUENCE: 7

Met Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser Ser
        35                  40                  45

Ser Arg Arg Arg Gly Ile Lys Ser Ser Pro Ser Ser Ile Ser Ala
50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
        115                 120                 125

Ala Leu Thr Arg Ser Ser Ile Arg Asn Val Leu Pro Arg His Glu
130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Pro Arg Arg Met Ile Gly Thr Asp Ala Phe Gln Glu
        195                 200                 205

Thr Pro Ile Val Glu Val Thr Arg Ser Ile Thr Lys His Asn Tyr Leu
210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
        275                 280                 285

Leu Glu Gln Ile Val Arg Leu Ile Ser Glu Ser Lys Lys Pro Val Leu
290                 295                 300
```

-continued

```
Tyr Val Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
            325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
            355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
            405                 410                 415

Leu Ala Leu Gln Gly Met Asn Lys Val Leu Glu Asn Arg Ala Glu Glu
            420                 425                 430

Leu Lys Leu Asp Phe Gly Val Trp Arg Asn Glu Leu Asn Val Gln Lys
            435                 440                 445

Gln Lys Phe Pro Leu Ser Phe Lys Thr Phe Gly Glu Ala Ile Pro Pro
450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
            485                 490                 495

Asn Tyr Lys Lys Pro Arg Arg Gln Trp Leu Ser Ser Gly Gly Leu Gly
            500                 505                 510

Ala Met Gly Phe Gly Leu Pro Ala Ala Ile Gly Ala Ser Val Ala Asn
            515                 520                 525

Pro Asp Ala Ile Val Val Asp Ile Asp Gly Asp Gly Ser Phe Ile Met
530                 535                 540

Asn Val Gln Glu Leu Ala Thr Ile Arg Val Glu Asn Leu Pro Val Lys
545                 550                 555                 560

Val Leu Leu Leu Asn Asn Gln His Leu Gly Met Val Met Gln Trp Glu
            565                 570                 575

Asp Arg Phe Tyr Lys Ala Asn Arg Ala His Thr Phe Leu Gly Asp Pro
            580                 585                 590

Ala Gln Glu Asp Glu Ile Phe Pro Asn Met Leu Leu Phe Ala Ala Ala
            595                 600                 605

Cys Gly Ile Pro Ala Ala Arg Val Thr Lys Lys Ala Asp Leu Arg Glu
610                 615                 620

Ala Ile Gln Thr Met Leu Asp Thr Pro Gly Pro Tyr Leu Leu Asp Val
625                 630                 635                 640

Ile Cys Pro His Gln Glu His Val Leu Pro Met Ile Pro Asn Gly Gly
            645                 650                 655

Thr Phe Asn Asp Val Ile Thr Glu Gly Asp Gly Arg Ile Lys Tyr
            660                 665                 670
```

<210> SEQ ID NO 8
<211> LENGTH: 652
<212> TYPE: PRT
<213> ORGANISM: Brassica napus

<400> SEQUENCE: 8

Met Ala Ala Ala Thr Ser Ser Ser Pro Ile Ser Leu Thr Ala Lys Pro

-continued

```
  1               5                    10                        15
Ser Ser Lys Ser Pro Leu Pro Ile Ser Arg Phe Ser Leu Pro Phe Ser
             20                  25              30

Leu Thr Pro Gln Lys Pro Ser Ser Arg Leu His Arg Pro Leu Ala Ile
         35                  40              45

Ser Ala Val Leu Asn Ser Pro Val Asn Val Ala Pro Glu Lys Thr Asp
     50                  55                  60

Lys Ile Lys Thr Phe Ile Ser Arg Tyr Ala Pro Asp Glu Pro Arg Lys
 65                  70                  75                  80

Gly Ala Asp Ile Leu Val Glu Ala Leu Glu Arg Gln Gly Val Glu Thr
                 85                  90                  95

Val Phe Ala Tyr Pro Gly Gly Ala Ser Met Glu Ile His Gln Ala Leu
                100                 105                 110

Thr Arg Ser Ser Thr Ile Arg Asn Val Leu Pro Arg His Glu Gln Gly
            115                 120                 125

Gly Val Phe Ala Ala Glu Gly Tyr Ala Arg Ser Ser Gly Lys Pro Gly
        130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
            180                 185                 190

Ile Val Glu Val Thr Arg Ser Ile Thr Lys His Asn Tyr Leu Val Met
        195                 200                 205

Asp Val Asp Asp Ile Pro Arg Ile Val Gln Glu Ala Phe Phe Leu Ala
    210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
            260                 265                 270

Gln Ile Val Arg Leu Ile Ser Glu Ser Lys Arg Pro Val Leu Tyr Val
        275                 280                 285

Gly Gly Gly Ser Leu Asn Ser Ser Glu Glu Leu Gly Arg Phe Val Glu
    290                 295                 300

Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Leu Ala Phe
            340                 345                 350

Gly Val Arg Phe Asp Asp Arg Val Thr Gly Lys Leu Glu Ala Phe Ala
        355                 360                 365

Ser Arg Ala Lys Ile Val His Ile Asp Ile Asp Ser Ala Glu Ile Gly
    370                 375                 380

Lys Asn Lys Thr Pro His Val Ser Val Cys Gly Asp Val Lys Leu Ala
385                 390                 395                 400

Leu Gln Gly Met Asn Lys Val Leu Glu Asn Arg Ala Glu Glu Leu Lys
                405                 410                 415

Leu Asp Phe Gly Val Trp Arg Ser Glu Leu Ser Glu Gln Lys Gln Lys
            420                 425                 430
```

```
Phe Pro Leu Ser Phe Lys Thr Phe Gly Glu Ala Ile Pro Pro Gln Tyr
            435                 440                 445

Ala Ile Gln Val Leu Asp Glu Leu Thr Gln Gly Lys Ala Ile Ile Ser
450                 455                 460

Thr Gly Val Gly Gln His Gln Met Trp Ala Ala Gln Phe Tyr Lys Tyr
465                 470                 475                 480

Arg Lys Pro Arg Gln Trp Leu Ser Ser Gly Leu Gly Ala Met Gly
                    485                 490                 495

Phe Gly Leu Pro Ala Ala Ile Gly Ala Ser Val Ala Asn Pro Asp Ala
                500                 505                 510

Ile Val Val Asp Ile Asp Gly Asp Gly Ser Phe Ile Met Asn Val Gln
            515                 520                 525

Glu Leu Ala Thr Ile Arg Val Glu Asn Leu Pro Val Lys Ile Leu Leu
530                 535                 540

Leu Asn Asn Gln His Leu Gly Met Val Met Gln Trp Glu Asp Arg Phe
545                 550                 555                 560

Tyr Lys Ala Asn Arg Ala His Thr Tyr Leu Gly Asp Pro Ala Arg Glu
                565                 570                 575

Asn Glu Ile Phe Pro Asn Met Leu Gln Phe Ala Gly Ala Cys Gly Ile
                580                 585                 590

Pro Ala Ala Arg Val Thr Lys Lys Glu Glu Leu Arg Glu Ala Ile Gln
            595                 600                 605

Thr Met Leu Asp Thr Pro Gly Pro Tyr Leu Leu Asp Val Ile Cys Pro
            610                 615                 620

His Gln Glu His Val Leu Pro Met Ile Pro Ser Gly Gly Thr Phe Lys
625                 630                 635                 640

Asp Val Ile Thr Glu Gly Asp Gly Arg Thr Lys Tyr
                    645                 650

<210> SEQ ID NO 9
<211> LENGTH: 637
<212> TYPE: PRT
<213> ORGANISM: Brassica napus

<400> SEQUENCE: 9

Met Ala Ser Phe Ser Phe Gly Thr Ile Pro Ser Ser Pro Thr Lys
 1               5                  10                  15

Ala Ser Val Phe Ser Leu Pro Val Ser Val Thr Thr Leu Pro Ser Phe
            20                  25                  30

Pro Arg Arg Arg Ala Thr Arg Val Ser Val Ser Ala Asn Ser Lys Lys
        35                  40                  45

Asp Gln Asp Arg Thr Ala Ser Arg Arg Glu Asn Pro Ser Thr Phe Ser
50                  55                  60

Ser Lys Tyr Ala Pro Asn Val Pro Arg Ser Gly Ala Asp Ile Leu Val
65                  70                  75                  80

Glu Ala Leu Glu Arg Gln Gly Val Asp Val Val Phe Ala Tyr Pro Gly
                85                  90                  95

Gly Ala Ser Met Glu Ile His Gln Ala Leu Thr Arg Ser Asn Thr Ile
            100                 105                 110

Arg Asn Val Leu Pro Arg His Glu Gln Gly Gly Ile Phe Ala Ala Glu
        115                 120                 125

Gly Tyr Ala Arg Ser Ser Gly Lys Pro Gly Ile Cys Ile Ala Thr Ser
130                 135                 140

Gly Pro Gly Ala Met Asn Leu Val Ser Gly Leu Ala Asp Ala Leu Phe
```

```
145                 150                 155                 160
Asp Ser Val Pro Leu Ile Ala Ile Thr Gly Gln Val Pro Arg Arg Met
                165                 170                 175
Ile Gly Thr Met Ala Phe Gln Glu Thr Pro Val Val Glu Val Thr Arg
            180                 185                 190
Thr Ile Thr Lys His Asn Tyr Leu Val Met Glu Val Asp Asp Ile Pro
        195                 200                 205
Arg Ile Val Arg Glu Ala Phe Phe Leu Ala Thr Ser Val Arg Pro Gly
    210                 215                 220
Pro Val Leu Ile Asp Val Pro Lys Asp Val Gln Gln Phe Ala Ile
225                 230                 235                 240
Pro Asn Trp Glu Gln Pro Met Arg Leu Pro Leu Tyr Met Ser Thr Met
                245                 250                 255
Pro Lys Pro Pro Lys Val Ser His Leu Glu Gln Ile Leu Arg Leu Val
            260                 265                 270
Ser Glu Ser Lys Arg Pro Val Leu Tyr Val Gly Gly Cys Leu Asn
        275                 280                 285
Ser Ser Glu Glu Leu Arg Arg Phe Val Glu Leu Thr Gly Ile Pro Val
    290                 295                 300
Ala Ser Thr Phe Met Gly Leu Gly Ser Tyr Pro Cys Asp Asp Glu Glu
305                 310                 315                 320
Phe Ser Leu Gln Met Leu Gly Met His Gly Thr Val Tyr Ala Asn Tyr
                325                 330                 335
Ala Val Glu Tyr Ser Asp Leu Leu Ala Phe Gly Val Arg Phe Asp
            340                 345                 350
Asp Arg Val Thr Gly Lys Leu Glu Ala Phe Ala Ser Arg Ala Lys Ile
        355                 360                 365
Val His Ile Asp Ile Asp Ser Thr Glu Ile Gly Lys Asn Lys Thr Pro
    370                 375                 380
His Val Ser Val Cys Cys Asp Val Gln Leu Ala Leu Gln Gly Met Asn
385                 390                 395                 400
Glu Val Leu Glu Asn Arg Arg Asp Val Leu Asp Phe Gly Glu Trp Arg
                405                 410                 415
Cys Glu Leu Asn Glu Gln Arg Leu Lys Phe Pro Leu Arg Tyr Lys Thr
            420                 425                 430
Phe Gly Glu Glu Ile Pro Pro Gln Tyr Ala Ile Gln Leu Leu Asp Glu
        435                 440                 445
Leu Thr Asp Gly Lys Ala Ile Ile Thr Thr Gly Val Gly Gln His Gln
    450                 455                 460
Met Trp Ala Ala Gln Phe Tyr Arg Phe Lys Lys Pro Arg Gln Trp Leu
465                 470                 475                 480
Ser Ser Gly Gly Leu Gly Ala Met Gly Phe Gly Leu Pro Ala Ala Met
                485                 490                 495
Gly Ala Ala Ile Ala Asn Pro Gly Ala Val Val Asp Ile Asp Gly
            500                 505                 510
Asp Gly Ser Phe Ile Met Asn Ile Gln Glu Leu Ala Thr Ile Arg Val
        515                 520                 525
Glu Asn Leu Pro Val Lys Val Leu Leu Ile Asn Asn Gln His Leu Gly
    530                 535                 540
Met Val Leu Gln Trp Glu Asp His Phe Tyr Ala Ala Asn Arg Ala Asp
545                 550                 555                 560
Ser Phe Leu Gly Asp Pro Ala Asn Pro Glu Ala Val Phe Pro Asp Met
                565                 570                 575
```

```
Leu Leu Phe Ala Ala Ser Cys Gly Ile Pro Ala Ala Arg Val Thr Arg
            580             585             590

Arg Glu Asp Leu Arg Glu Ala Ile Gln Thr Met Leu Asp Thr Pro Gly
        595             600             605

Pro Phe Leu Leu Asp Val Val Cys Pro His Gln Asp His Val Leu Pro
    610             615             620

Leu Ile Pro Ser Gly Gly Thr Phe Lys Asp Ile Ile Val
625             630             635
```